(12) United States Patent
Addison et al.

(10) Patent No.: US 8,696,585 B2
(45) Date of Patent: *Apr. 15, 2014

(54) DETECTING A PROBE-OFF EVENT IN A MEASUREMENT SYSTEM

(75) Inventors: Paul Stanley Addison, Edinburgh (GB); James Nicholas Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1573 days.

This patent is subject to a terminal disclaimer.

(21) Appl. No.: 12/242,894

(22) Filed: Sep. 30, 2008

(65) Prior Publication Data

US 2010/0081898 A1    Apr. 1, 2010

(51) Int. Cl.
  *A61B 5/02*    (2006.01)
  *A61B 8/14*    (2006.01)
(52) U.S. Cl.
  USPC ............ 600/500; 600/502; 600/504; 600/459
(58) Field of Classification Search
  None
  See application file for complete search history.

(56) References Cited

U.S. PATENT DOCUMENTS

| | | | |
|---|---|---|---|
| 4,289,141 | A | 9/1981 | Cormier |
| 5,319,355 | A | 6/1994 | Russek |
| 5,353,799 | A | 10/1994 | Chance |
| 5,439,483 | A | 8/1995 | Duong-Van |
| 5,590,650 | A | 1/1997 | Genova |
| 5,632,272 | A | 5/1997 | Diab et al. |
| 5,778,881 | A | 7/1998 | Sun et al. |
| 5,795,304 | A | 8/1998 | Sun et al. |
| 5,797,840 | A | 8/1998 | Akselrod |
| 5,827,195 | A | 10/1998 | Lander |
| 5,846,190 | A | 12/1998 | Woehrle |
| 5,967,995 | A | 10/1999 | Shusterman et al. |
| 6,002,952 | A | 12/1999 | Diab et al. |
| 6,036,653 | A | 3/2000 | Baba et al. |
| 6,094,592 | A | 7/2000 | Yorkey |
| 6,095,984 | A | 8/2000 | Amano et al. |
| 6,117,075 | A | 9/2000 | Barnea |
| 6,129,675 | A | 10/2000 | Jay |
| 6,135,966 | A | 10/2000 | Ko |
| 6,171,257 | B1 | 1/2001 | Weil et al. |
| 6,171,258 | B1 | 1/2001 | Karakasoglu et al. |
| 6,208,951 | B1 | 3/2001 | Kumar et al. |
| 6,293,915 | B1 | 9/2001 | Amano et al. |
| 6,325,761 | B1 | 12/2001 | Jay |
| 6,360,114 | B1 | 3/2002 | Diab et al. |
| 6,361,501 | B1 | 3/2002 | Amano et al. |
| 6,393,311 | B1 | 5/2002 | Edgar, Jr. et al. |
| 6,449,501 | B1 | 9/2002 | Reuss |
| 6,510,329 | B2 | 1/2003 | Heckel |
| 6,561,986 | B2 | 5/2003 | Baura |
| 6,606,510 | B2 | 8/2003 | Swedlow et al. |
| 6,606,511 | B1 | 8/2003 | Ali et al. |
| 6,608,934 | B2 | 8/2003 | Scheirer |
| 6,654,623 | B1 | 11/2003 | Kastle |
| 6,654,624 | B2 | 11/2003 | Diab et al. |
| 6,675,031 | B1 | 1/2004 | Porges et al. |
| 6,771,994 | B2 | 8/2004 | Kiani et al. |
| 6,810,277 | B2 | 10/2004 | Edgar, Jr. et al. |
| 6,822,564 | B2 | 11/2004 | Al-Ali |
| 6,898,452 | B2 | 5/2005 | Al-Ali et al. |
| 6,931,269 | B2 | 8/2005 | Terry |
| 6,987,994 | B1 | 1/2006 | Mortz |
| 6,993,377 | B2 | 1/2006 | Flick et al. |
| 7,001,337 | B2 | 2/2006 | Dekker |
| 7,006,856 | B2 | 2/2006 | Baker, Jr. et al. |
| 7,020,507 | B2 | 3/2006 | Scharf |
| 7,024,233 | B2 | 4/2006 | Ali et al. |
| 7,035,679 | B2 | 4/2006 | Addison et al. |
| 7,043,293 | B1 | 5/2006 | Baura |
| 7,054,453 | B2 | 5/2006 | Causevic et al. |
| 7,054,454 | B2 | 5/2006 | Causevic et al. |
| 7,079,888 | B2 | 7/2006 | Oung |
| 7,171,269 | B1 | 1/2007 | Addison |
| 7,173,525 | B2 | 2/2007 | Albert |
| 7,194,293 | B2 | 3/2007 | Baker, Jr. |

(Continued)

FOREIGN PATENT DOCUMENTS

JP    09-084776    3/1997
WO    WO 01/025802    4/2001

(Continued)

OTHER PUBLICATIONS

Addison, Paul S., The Illustrated Wavelet Transform Handbook, Taylor & Francis Group, 2002.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

(Continued)

*Primary Examiner* — Benjamin P Blumel

(57) ABSTRACT

According to embodiments, techniques for detecting probe-off events are disclosed. A sensor or probe may be used to obtain a plethysmograph or photoplethysmograph (PPG) signal from a subject. A wavelet transform of the signal may be performed and a scalogram may be generated based at least in part on the wavelet transform. One or more characteristics of the scalogram may be determined. The determined characteristics may include, for example, an energy decrease, a broad-scale high-energy cone, a regular, repeated high-scale pattern, a low-scale information pattern; and a pulse band. The absence or presence of these and other characteristics, along with information about the characteristics, may be analyzed to detect a probe-off event. A confidence indicator may be calculated in connection with probe-off event detections and alarms may be generated when probe-off events occur.

20 Claims, 20 Drawing Sheets

(2 of 20 Drawing Sheet(s) Filed in Color)

(56) References Cited

U.S. PATENT DOCUMENTS

| | | |
|---|---|---|
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,355,512 B1 | 4/2008 | Al-Ali |
| 7,457,652 B2 | 11/2008 | Porges et al. |
| 7,471,969 B2 | 12/2008 | Diab et al. |
| 7,477,571 B2 | 1/2009 | Melese et al. |
| 7,499,835 B2 | 3/2009 | Weber et al. |
| 7,515,949 B2 | 4/2009 | Norris |
| 7,519,488 B2 | 4/2009 | Fu |
| 7,523,011 B2 | 4/2009 | Akiyama et al. |
| 7,566,306 B2 | 7/2009 | Fujiwara et al. |
| 2004/0158134 A1 | 8/2004 | Diab et al. |
| 2005/0043616 A1 | 2/2005 | Chinchoy |
| 2005/0070774 A1* | 3/2005 | Addison et al. ............... 600/323 |
| 2006/0122476 A1 | 6/2006 | Van Slyke |
| 2006/0211930 A1 | 9/2006 | Scharf et al. |
| 2006/0220881 A1 | 10/2006 | Al-Ali et al. |
| 2006/0226992 A1 | 10/2006 | Al-Ali et al. |
| 2006/0238358 A1 | 10/2006 | Al-Ali et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0043269 A1 | 2/2007 | Mannheimer et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0208259 A1 | 9/2007 | Mannheimer |
| 2007/0282212 A1 | 12/2007 | Sierra et al. |
| 2008/0039699 A1 | 2/2008 | Neumann |
| 2008/0045832 A1 | 2/2008 | McGrath |
| 2008/0081971 A1 | 4/2008 | Ollerdessen |
| 2008/0082018 A1 | 4/2008 | Sackner et al. |
| 2008/0091092 A1 | 4/2008 | Al-Ali |
| 2008/0091093 A1 | 4/2008 | Al-Ali |
| 2008/0109041 A1 | 5/2008 | De Voir |
| 2008/0214903 A1 | 9/2008 | Orbach |
| 2008/0221418 A1 | 9/2008 | Al-Ali et al. |
| 2008/0242955 A1 | 10/2008 | Uutela et al. |
| 2008/0243021 A1 | 10/2008 | Causevic et al. |
| 2010/0016691 A1* | 1/2010 | Watson et al. ............... 600/323 |
| 2010/0079279 A1* | 4/2010 | Watson et al. ............... 340/540 |

FOREIGN PATENT DOCUMENTS

| | | |
|---|---|---|
| WO | WO 01/062152 | 8/2001 |
| WO | WO 03/055395 | 7/2003 |
| WO | 2004/075746 A2 | 9/2004 |
| WO | WO 2004/105601 | 12/2004 |
| WO | WO 2005/096170 | 10/2005 |
| WO | WO 2006/085120 | 8/2006 |
| WO | 2007/131173 A2 | 11/2007 |

OTHER PUBLICATIONS

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R.,.Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

* cited by examiner

DETECTING A PROBE-OFF EVENT IN A MEASUREMENT SYSTEM

SUMMARY

The present disclosure relates to signal processing and, more particularly, the present disclosure relates to using characteristics of one or more wavelet scalograms of a signal, such as a photoplethysmograph (PPG) signal, to determine if a probe-off event has occurred in a system, such as a pulse oximetry system.

In an embodiment, a pulse oximeter system is used to measure and analyze physiological signals produced by a patient. The pulse oximeter may be used to measure the oxygen saturation in blood, changes in blood volume in tissue, and the pulse rate of a patient. The pulse oximeter may display various patient characteristics including, but not limited to, the oxygen saturation of hemoglobin in arterial blood. To collect measurements, the pulse oximeter may use a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time is referred to as a PPG signal. A probe-off event occurs when the target stimulus (e.g., a patient fingertip, toe, forehead, earlobe, or foot) is no longer reflected in measurement of the PPG signal. Possible causes of such a probe-off event include: the patient removing the sensor, the sensor being accidentally dislodged, or the sensor or any constituent component of the sensor being damaged or otherwise malfunctioning.

In an embodiment, a PPG signal is transformed using a continuous wavelet transform. Information derived from the continuous wavelet transform of the PPG signal may be used to provide measurements of one or more physiological parameters. The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In an embodiment, one or more scalograms may be obtained by processing the wavelet transform. Each scalogram may represent the energy density of the PPG signal, where a suitable scaling has been performed to emphasize certain scale values or ranges of interest for the analysis of the PPG signal. The scalogram may be taken to include all suitable forms of rescaling including, but not limited to, the original unsealed wavelet representation, linear rescaling, any power of the modulus of the wavelet transform, or any other suitable resealing. In addition, the scalogram may contain information on the real part of the wavelet transform, the imaginary part of the wavelet transform, the phase of the wavelet transform, any other suitable part of the wavelet transform, or any combination thereof.

In an embodiment, characteristics of the one or more scalograms are determined and analyzed to determine if a probe-off event has occurred. These characteristics may be chosen based on a pre-existing knowledge of features that are expected in a scalogram before, during, and after a probe-off event. For example, before a probe-off event occurs several common characteristics may occur that can be identified on the basis of the energy level and structure present in the one or more scalograms. These characteristics may include the presence of a pulse band (a band of relatively constant energy over a range of scale values), and a regular, repeated high-scale information pattern (a oscillatory pattern of energy fluctuations in time, and at a certain range of scale values). Similarly, certain characteristics indicate the occurrence of a probe-off event. For example, a probe-off event is known to produce a broadscale high-energy cone in the scalogram (a cone-shaped region of high energy, with a width that decreases as the scale value increases). Detection processes are used to determine which of these events, if any, are present in the one or more scalograms.

In an embodiment, the detection process described above returns both a binary decision (either "detected" or "not detected"), as well as a probability or confidence indicator in the detection result, for each characteristic of interest. One or more of detection results and probability or confidence indicators may be weighed according to one or more processes so that a final, single decision is made as to the occurrence of a probe-off event. If it is determined that a probe-off event has occurred, a signal can be triggered. For example, the triggered signal can sound an alarm or display one or more on-screen messages to alert the user of the probe-off event. If it is determined that the probe-off event has not occurred, then the detection process returns to a state where the next portion of a scalogram is analyzed for characteristics.

BRIEF DESCRIPTION OF THE DRAWINGS

The patent or application file contains at least one drawing executed in color. Copies of this patent or patent application publication with color drawing(s) wilt be provided by the Office upon request and payment of the necessary fee The above and other features of the present disclosure, its nature and various advantages will be more apparent upon consideration of the following detailed description, taken in conjunction with the accompanying drawings in which.

DETAILED DESCRIPTION

Figure 1:
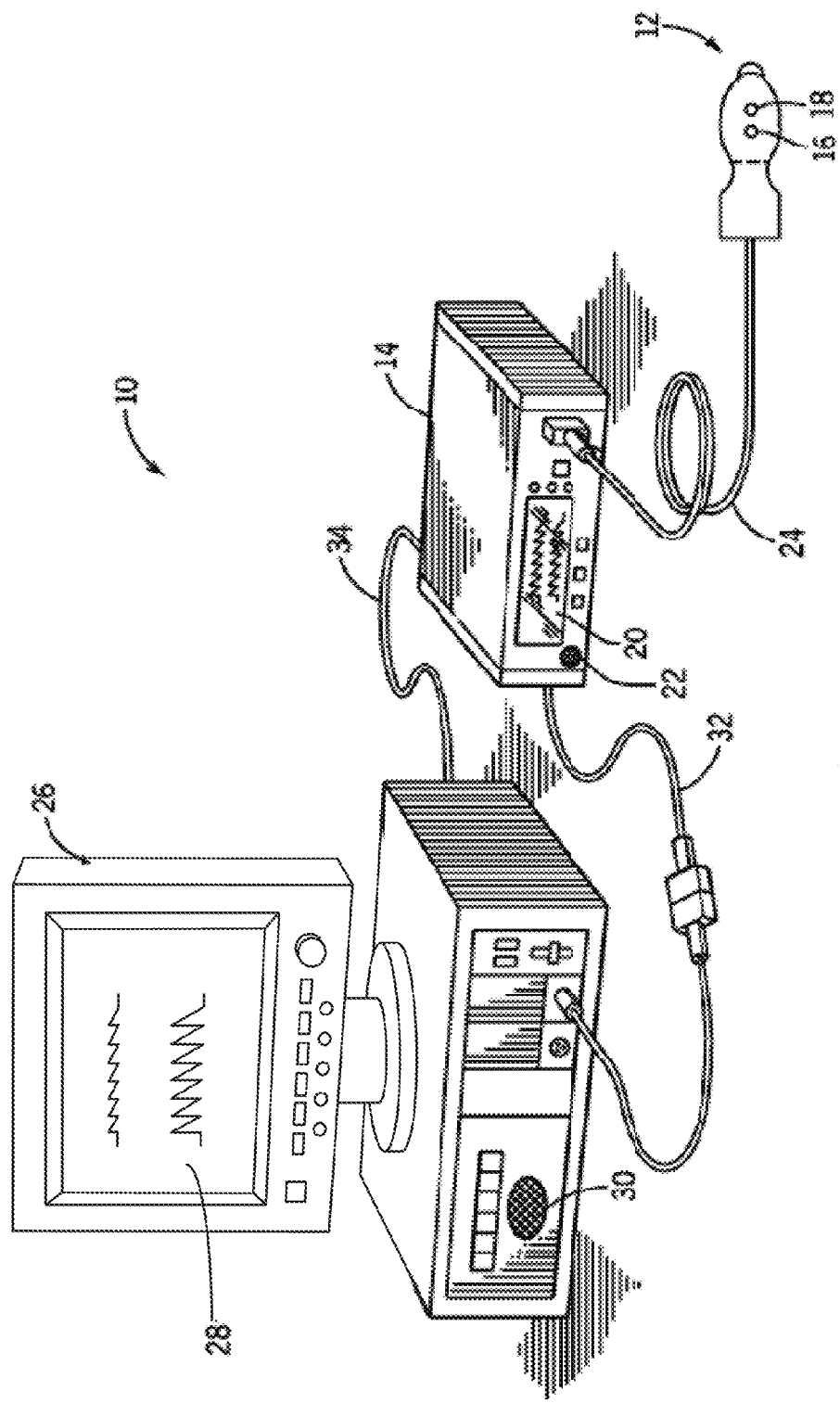
FIG. 1 shows an illustrative pulse oximetry system in accordance with an embodiment.

The present disclosure relates to signal processing and, more particularly, the present disclosure relates to using characteristics of one or more wavelet scalograms of a signal, such as a photoplethysmograph (PPG) signal, to determine if a probe-off event has occurred in a system, such as a pulse oximetry system.

In medicine, a plethysmograph is an instrument that measures physiological parameters, such as variations in the size of an organ or body part, through an analysis of the blood passing through or present in the targeted body part, or a depiction of these variations. An oximeter is an instrument that may determine the oxygen saturation of the blood. One common type of oximeter is a pulse oximeter, which determines oxygen saturation by analysis of an optically sensed plethysmograph.

A pulse oximeter is a medical device that may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

The optical signal through the tissue can be degraded by noise, among other sources. One source of noise is ambient light which reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, since blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
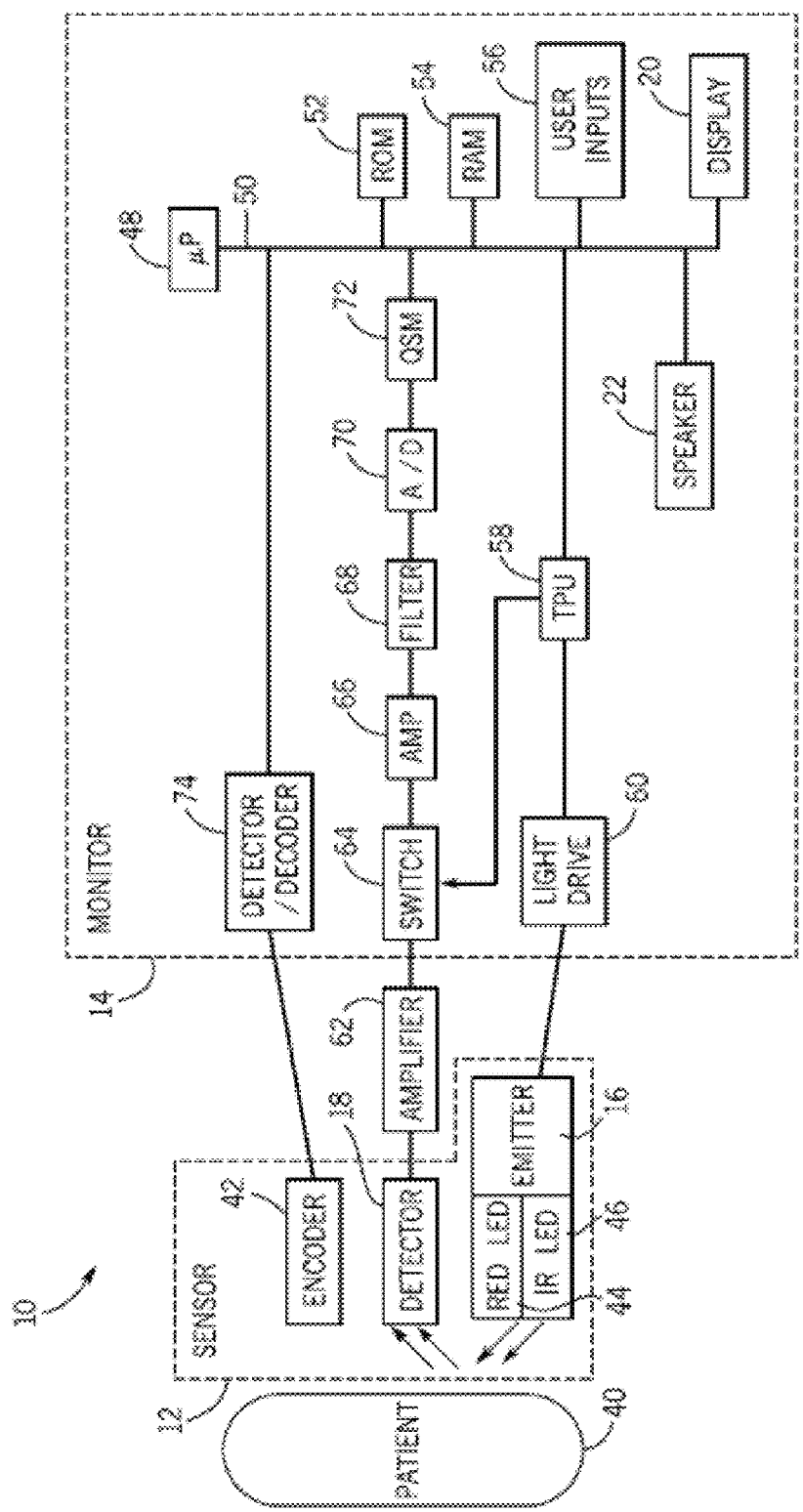
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14; the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise can degrade a pulse oximetry signal relied upon by a physician, without the physicians awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \tag{9}$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \tag{10}$$

where '||' is the modulus operator. The scalogram may be resealed for useful purposes. One common resealing is defined as $$S_R(a, b) = \frac{|T(a, b)|^2}{a} \tag{11}$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear resealing, any power of the modulus of the wavelet transform, or any other suitable resealing. In addition, for purposes of clarity and conciseness, the term "scalogram" shall be taken to mean the wavelet transform, $T(a,b)$ itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \tag{12}$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{j2\pi f_0 t} - e^{-(2\pi f_0)^2/2})e^{-t^2/2} \tag{13}$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \tag{14}$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
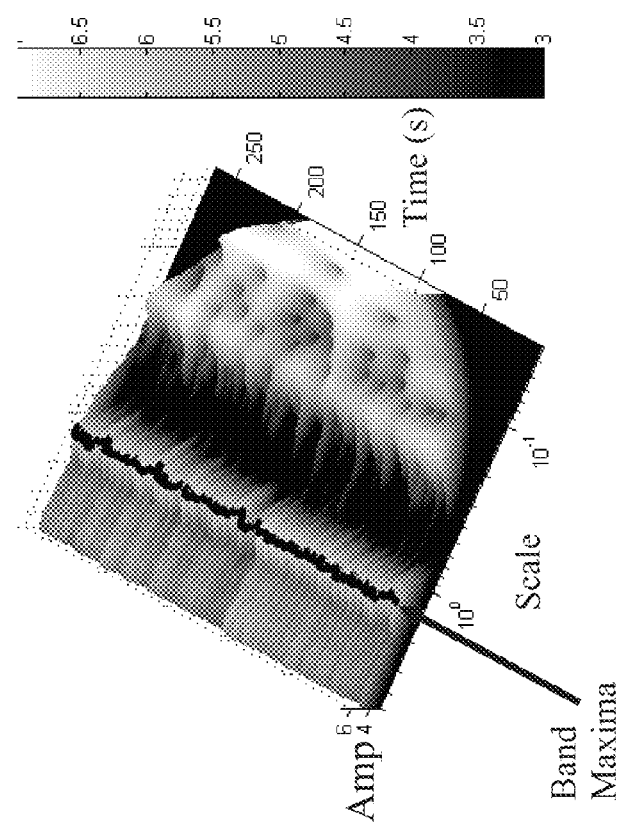
FIGS. 3(a) and 3(b) show illustrative views of a scalogram derived from a PPG signal in accordance with an embodiment.
Figure 3A:
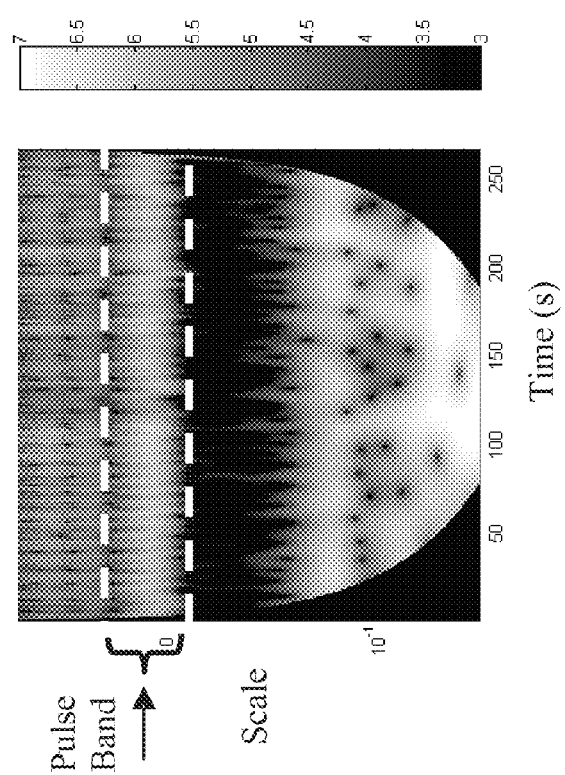

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures shows an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
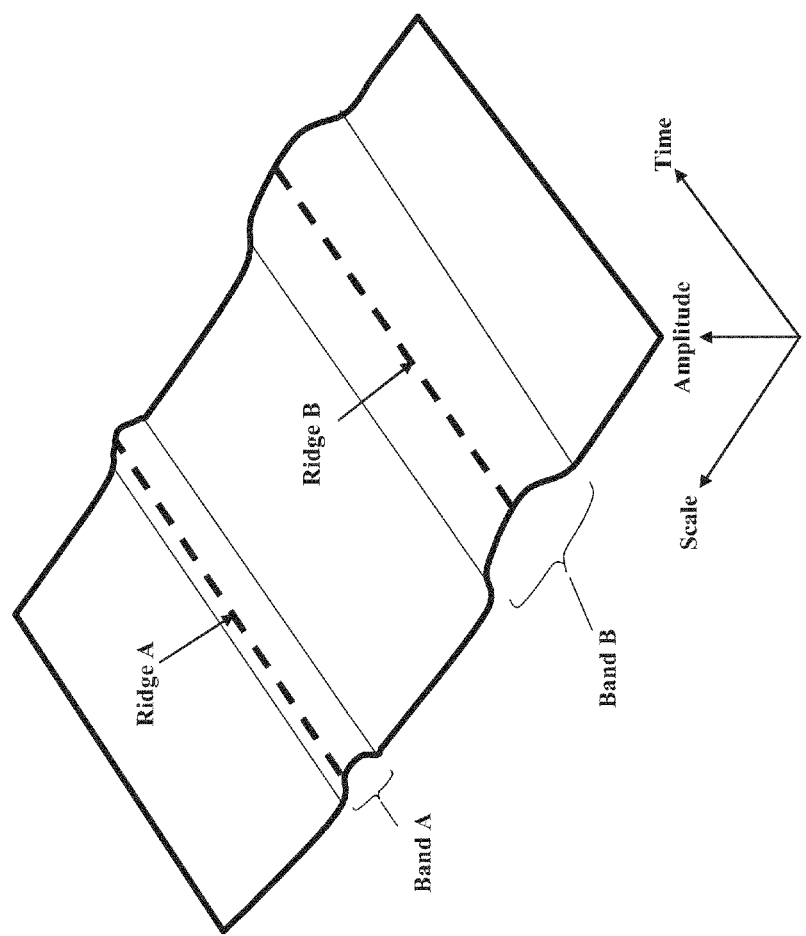
FIG. 3(c) shows an illustrative scalogram derived from a signal containing two pertinent components in accordance with an embodiment.
Figure 3D:
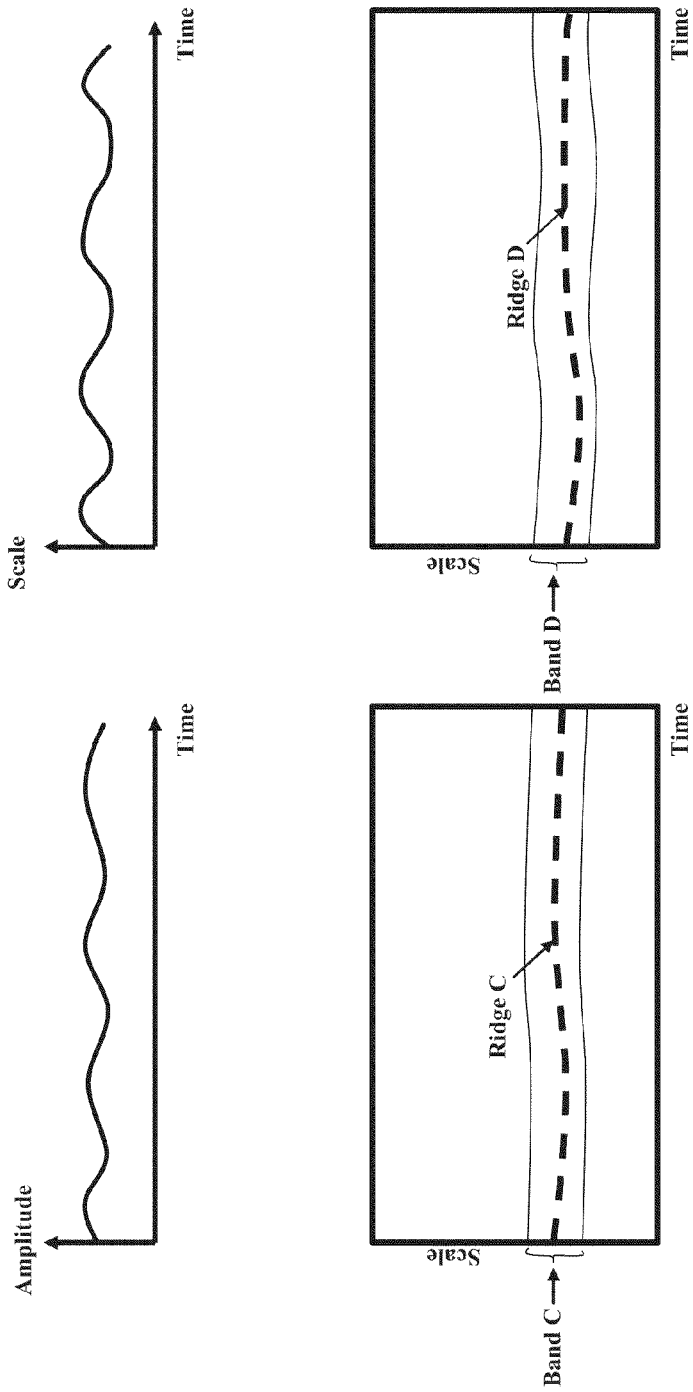
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
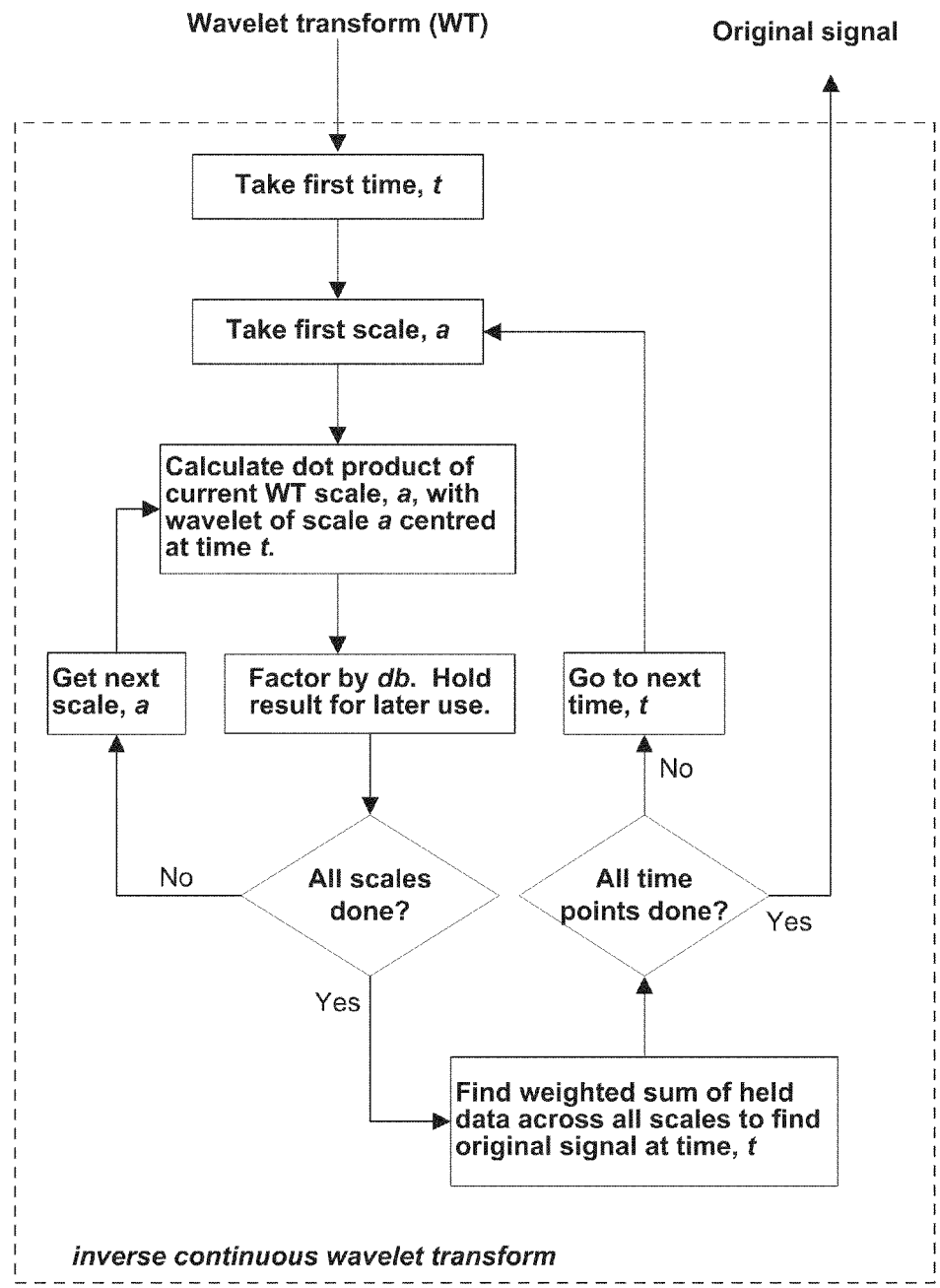
FIGS. 3(e) and 3(f) are flow charts of illustrative steps involved in performing an inverse continuous wavelet transform in accordance with embodiments.
Figure 3F:
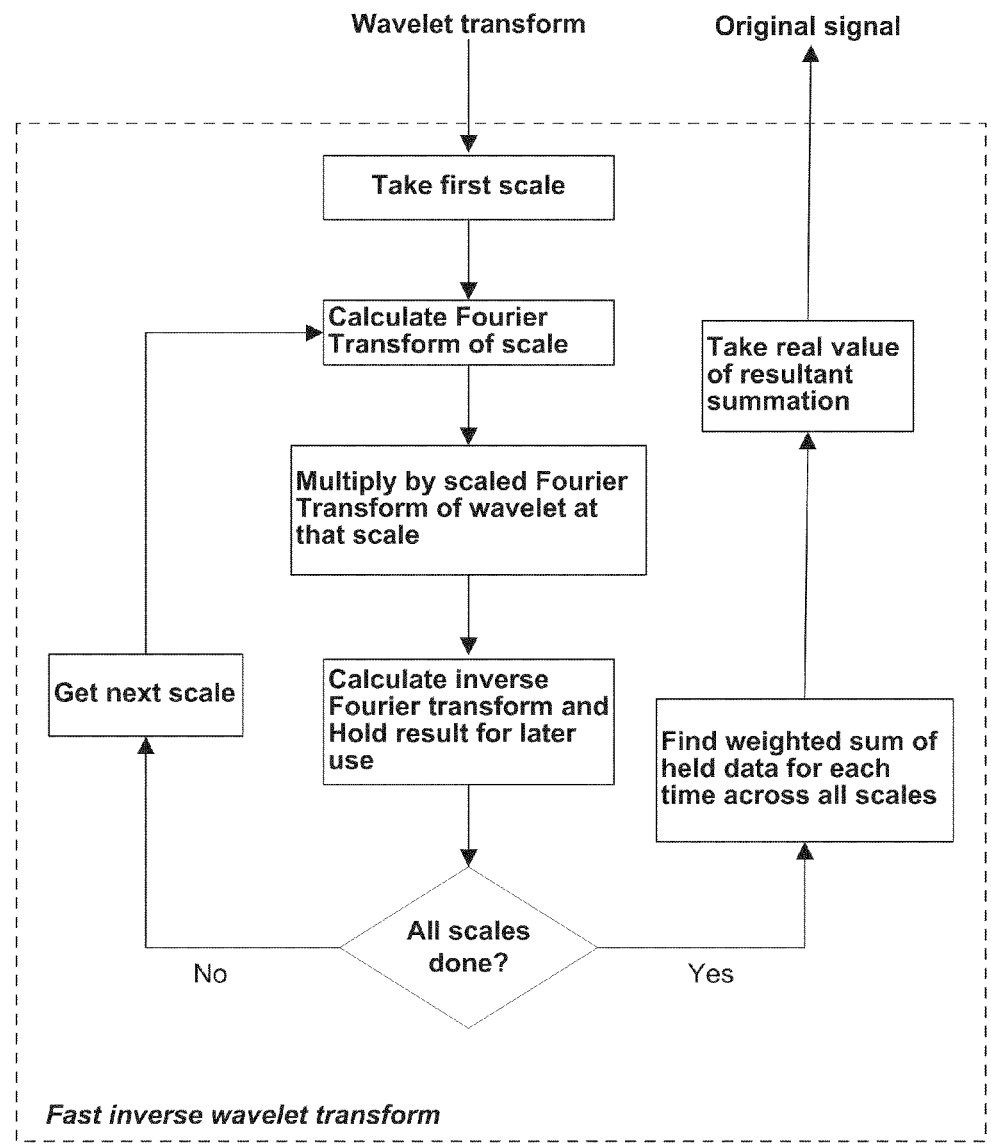

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
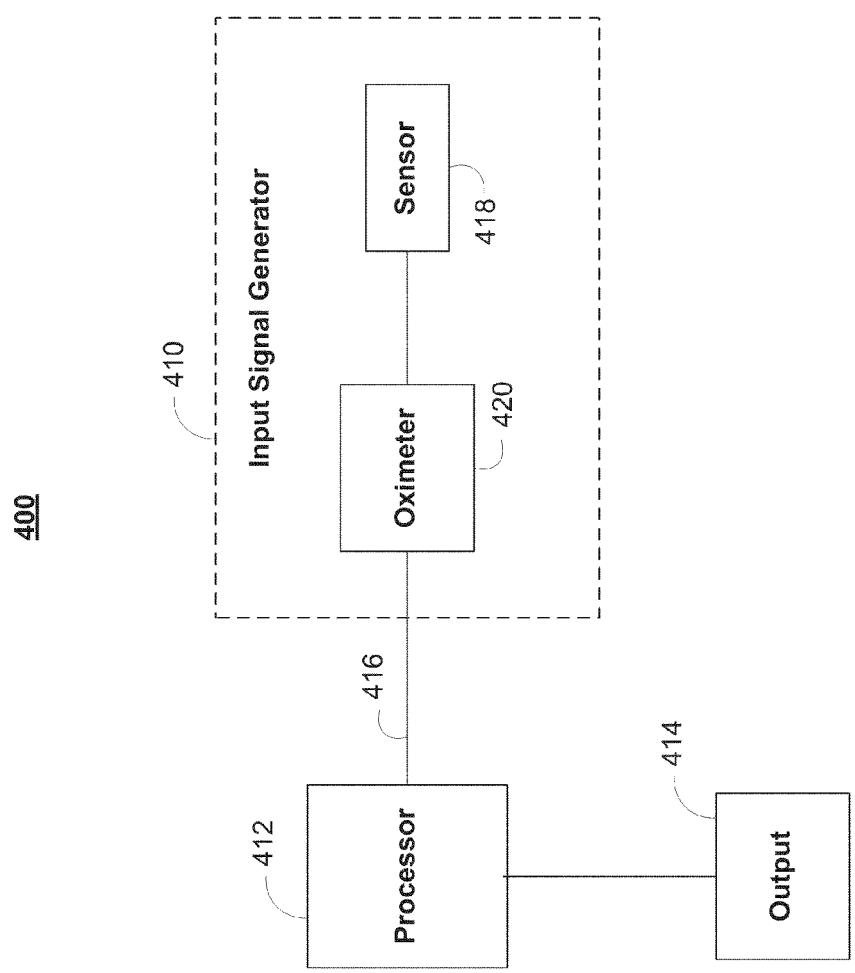
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
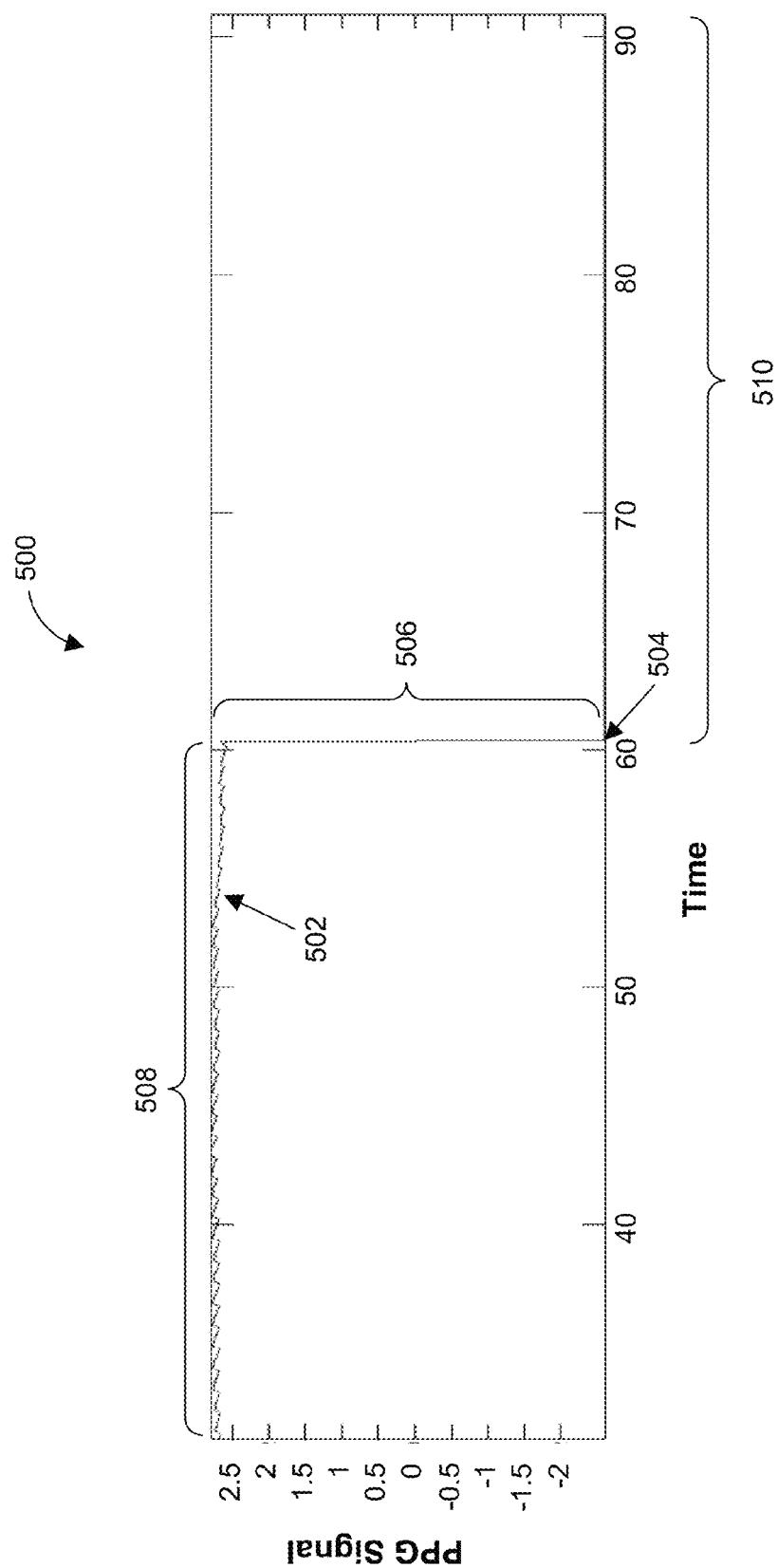
FIG. 5 is an illustrative plot of a PPG signal taken before, during, and after a probe-off event in accordance with an embodiment.

FIG. 5 is an illustrative plot of PPG signal 502 taken before, during, and after a probe-off event in accordance with an embodiment of the disclosure. Plot 500 displays time on the x-axis and values of the PPG signal 502 on the y-axis. PPG signal 502 may be obtained, for example, from sensor 12 (FIG. 1) or from averaging or otherwise combining a plurality of signals derived from a suitable sensor array, as discussed in relation to FIG. 1. Plot 500 may be displayed using any suitable display device such as, for example, monitor 20 (FIG. 1), display 28 (FIG. 1), a PDA, a mobile phone, or any other suitable display device. Additionally, plot 500 may be displayed on multiple display devices, or it may not be displayed on any display devices.

A probe-off event is an event wherein the target stimulus (e.g., a patient fingertip, toe, forehead, earlobe, or foot) is no longer reflected in measurement of the PPG signal 502. Possible causes of a probe-off event may include: the patient removing the sensor, the sensor being accidentally dislodged, the sensor or any constituent component of the sensor being damaged or otherwise malfunctioning, or a connecting cable (e.g., cable 24, 32, or 34 of FIG. 1) being removed or otherwise malfunctioning. PPG signal 502 is received during time period 508, which corresponds to the time before the probe-off event occurs. At approximately time 504, the probe-off event occurs. The probe-off event may result in a large and rapid change 506 in the value of PPG signal 502. As shown in FIG. 5, rapid change 506 is a large and rapid decrease in value of PPG signal 502. The probe-off event may have occurred at time 504 or at an earlier time, as the signal processing processes and circuitry may delay the appearance of signal value decrease 506. The actual signal value change may be more rapid or more gradual than the illustrative signal value decrease 506. The PPG signal is seen to have an approximately constant and relatively small signal value during time period 510, which corresponds to the time period after the prove-off event occurs.

Plot 500 was generated by removing a sensor such as sensor 12 (FIG. 1) or sensor 418 (FIG. 4) from a patient finger approximately half way through the data acquisition period shown by the x-axis in FIG. 1. However, as emphasized above, plot 500 is merely illustrative of a general PPG signal that may be obtained from, for example, pulse oximetry system 10 (FIG. 1) or system 400 (FIG. 4). Further, and as emphasized above, the target stimulus need not correspond to a patient finger, as many other target stimuli would produce a plot substantially similar to plot 500.

Figure 6:
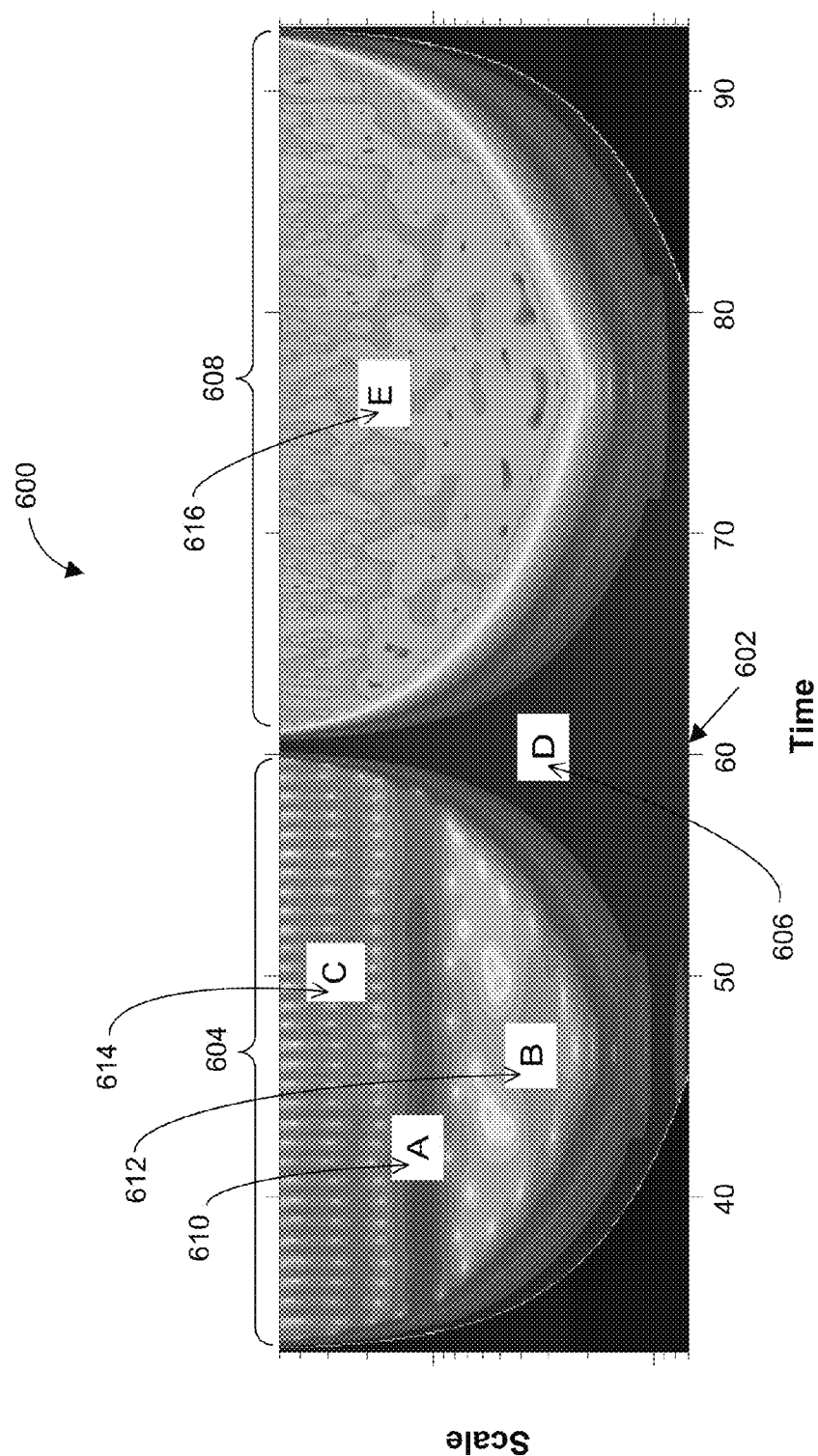
FIG. 6 shows an illustrative scalogram derived from the PPG signal of FIG. 5 in accordance with an embodiment.

FIG. 6 shows an illustrative scalogram 600 derived from a PPG signal such as PPG signal 502 (FIG. 5) before, during, and after a probe-off event in accordance with an embodiment. In scalogram 600, the x-axis of denotes time and the y-axis denotes scale. Time 602 may be equivalent to time 504 (FIG. 5). Thus, the probe-off event may occur at time 602 or at an earlier time. Scalogram 600 comprises three regions: region 604 corresponds to the time period for which the effect of the target stimulus is properly captured in the measurement of PPG signal 502 (FIG. 5), region 606 corresponds to the probe-off event, and region 608 corresponds to the time period after which the effect of the target stimulus is no longer properly captured in measurement of the PPG signal. In scalogram 600, "hotter" colors (e.g., hues of red, orange and yellow) correspond to larger energy values, while "cooler" colors (e.g., hues of blue and green) correspond to smaller energy values. Dark red (e.g., the color of the region surrounding 606) represents the largest energy value in the plot, whereas dark blue (e.g., the lower left of scalogram 600) represents the smallest energy value in the plot. Therefore, the region surrounding 606 (which consists of dark red colors) is the highest energy region in the plot, region 604 (which consists of light red and yellow colors) is a moderate energy region, region 608 (which consists of light blue and green colors) is a low energy region. The regions in the lower left and lower right of the plot are the "edge regions"—these have been set to the lowest value of the scalogram 606 plot. These regions have been added to mask out edge effects—the distortion of the scalogram component values around its leading and trailing edges caused by the signal under analysis not being of infinite length and thus containing an apparently abrupt change in values at its start and end. They are therefore features of the viewing window and, unlike region 606 which changes in time as the sensor signal changes, the edge regions remain of fixed value in the plot. The edge regions do not form part of the analyzed scalogram used within the method detailed herein.

Region 604 is distinguishable from region 606 and region 608 on the basis of its energy level and richly structured characteristics. Region 604 comprises a moderate-energy region, whereas region 606 comprises a high-energy region and region 608 comprises a low-energy region. Also, region 604 comprises a highly-structured region in scale values and in time, whereas region 606 is nearly featureless, and region 608 has only slowly varying, and random features and patterns.

In addition to the general trends described above, region 604 may include several unique identifying characteristics. Pulse band 610 may be present in region 604. Pulse band 610 may be caused by the pulse component of PPG signal 502 (FIG. 5), and may be identifiable by a moderate-energy component at a specified, possibly known range of scale values, surrounded by areas of lower energy. Low-frequency information pattern 612 may be present in region 604. Low frequency information pattern 612 may be caused by various regular and slowly changing phenomena, such as blood pressure variations, respiration, and slowly-varying patient movement, and may be identifiable by moderate energy values and structural characteristics. Regular, repeated high-scale pattern 614 may be present in region 604. Regular, repeated high-scale pattern 614 may be caused by pulses contained in PPG signal 502 (FIG. 5) and their constituent components, for example, the dicrotic notch, being resolved at smaller scales. Regular, repeated high-scale pattern 614 may be identified by regular, rapid oscillations between two moderate or high-energy levels over an extended period of time.

Region 606 comprises a distinct "cone-shaped" pattern centered about time 602. This pattern is caused by the changing width of the wavelet being applied at each scale. Consider any fixed scale value. When a probe-off event occurs, PPG signal 502 (FIG. 5) may change extremely rapidly in time, as discussed in relation to FIG. 5. It is known from wavelet theory that a large range of scales and large amount of energy is required to represent rapid signal transitions in time. This explains the high-energy values separating region 604 and 608 for all scales. As discussed above, its conical morphology is caused by the changing width of the wavelet being applied at each scale. As the scale value increases, the wavelet widths, also known as their temporal support, increase, and thus the width of the high-energy region of the scalogram increases. This cone-shaped feature's precise morphology is therefore strongly influenced by the wavelet being employed. It will hereafter be known as a "broadscale high-energy cone." Such a feature may be used to identify the probe-off event. For example, one method to detect the presence or absence of region 606 would be to detect the presence of a moderate energy region, followed by a high-energy region, followed by a low-energy region. Further, such a process may also compare the morphology of the candidate high energy region with that expected of a broadscale high-energy cone to improve accuracy of detection.

Region 608 corresponds to the time period after which a probe off event occurs. Region 608 may be characterized by an unstructured distribution of energy values (for example, see the area surrounding point 616), and significantly lower energy levels than those found in region 604 or region 606. Thus, by monitoring the energies in the scalogram and/or their regularity, an indication of the removal of a probe, i.e., a probe-off event, may be made. The shape of a high-energy feature or characteristics may serve as an indication of probe removal. For example, a probe-off event could be indicated or detected by detecting regularity in a scalogram at one or more times prior to the presence of a characteristic, following by detecting non-regularity in the scalogram at one or more times subsequent to the presence of the characteristic.

Figure 7:
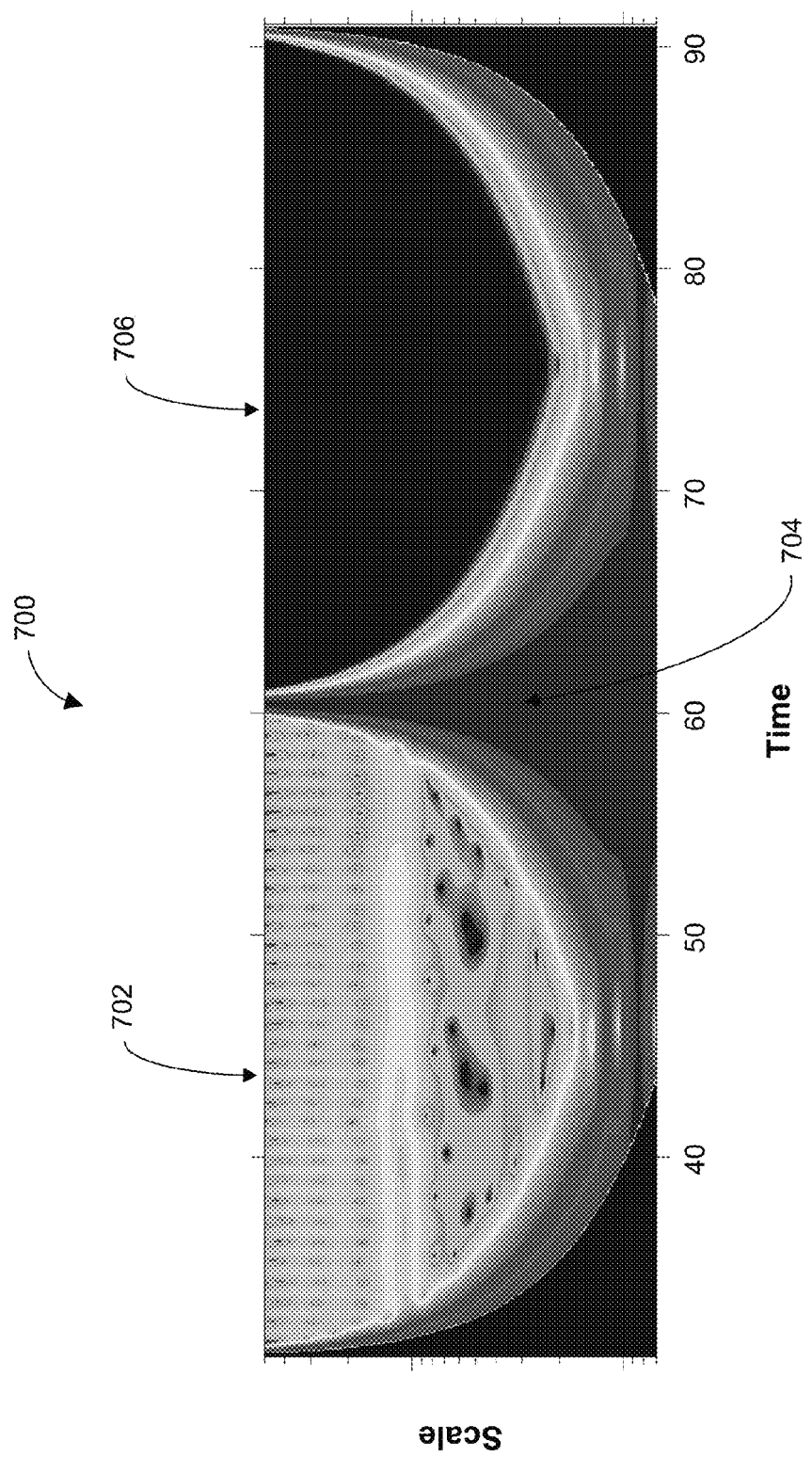
FIG. 7 shows an illustrative quantized scalogram derived from a PPG signal before, during, and after the probe-off event in accordance with an embodiment.

FIG. 7 shows an illustrative quantized scalogram derived from a PPG signal before, during, and after the probe-off event in accordance with an embodiment. Scalogram 700 is a quantized version of scalogram 600 (FIG. 6). Scalogram 700 may be obtained, for example, from an analysis of scalogram 600, or from a direct analysis of PPG signal 502 (FIG. 5). The axes values and the relative values of the colors in scalogram 700 are the same as for scalogram 600 (FIG. 6). In scalogram 700, region 706 is the region of the smallest energy, region 704 (consisting of a dark red color) is the region of the largest energy, and region 702 (consisting mostly of yellow and light blue colors, in addition to small amounts of dark blue color) is a region of moderate energy Again, the regions on the lower-right and lower left of the plot are edge effect regions which have been artificially set to a low value and are ignored in subsequent analysis. To obtain scalogram 700, each energy value in scalogram 600 (FIG. 6) was compared to a certain, fixed threshold. If an energy value was above the threshold then the energy value was preserved in translation from scalogram 600 (FIG. 6) to scalogram 700. If the energy value was equal to or below the threshold, then the energy value was replaced by the threshold value in scalogram 700. Notice that the exact energy values represented by the color scale is different in scalogram 600 (FIG. 6) than in scalogram 700 (for example, a particular shade of red may represent a different energy value in scalogram 600 (FIG. 6) than in scalogram 700). The color scale in each scalogram has been computed separately based on the range between the lowest and highest energy values in each scalogram. In scalogram 700, energy values below a threshold value located in the probe off region 706 have been set to the value of the threshold. This has increased the minimum energy value of scalogram 700 to a value higher than the minimum energy value in scalogram 600 (FIG. 6), and the color scale has been rescaled accordingly.

The pertinent features of scalogram 600 (FIG. 6) for detecting a probe-off event are preserved in scalogram 700. For example, scalogram 700 comprises three broad regions: Region 702 corresponds to the time period for which the effect of the target stimulus is properly captured in the measurement of PPG signal 502 (FIG. 5), region 704 corresponds to the probe-off event, and region 706 corresponds to the time period after which the effect of the target stimulus is no longer properly captured in measurement of the PPG signal. However, note that the lower-valued energy levels in scalogram 600 (FIG. 6) have been replaced with a single threshold value (denoted by dark blue) in scalogram 700. For example, region 608 (FIG. 6) comprises a low-energy region with energy values that are largely below the threshold value. These values have been replaced by a single threshold value, as seen in region 706.

The quantization scheme discussed above is merely one embodiment of a quantization scheme, and other schemes are possible. For example, scalogram 600 (FIG. 6) may be quantized by using two thresholds or multiple thresholds, wherein the quantized scalogram is obtained by rounding energy values of the original scalogram to the nearest threshold value. In addition, the number and value of quantization levels may be chosen based on the dynamic range of scalogram 600 (FIG. 6), the computational resources available, or based on a combination of these and many other factors. Also, each threshold could be a variable quantity that varies with, for example, the time or scale value.

Figure 8:
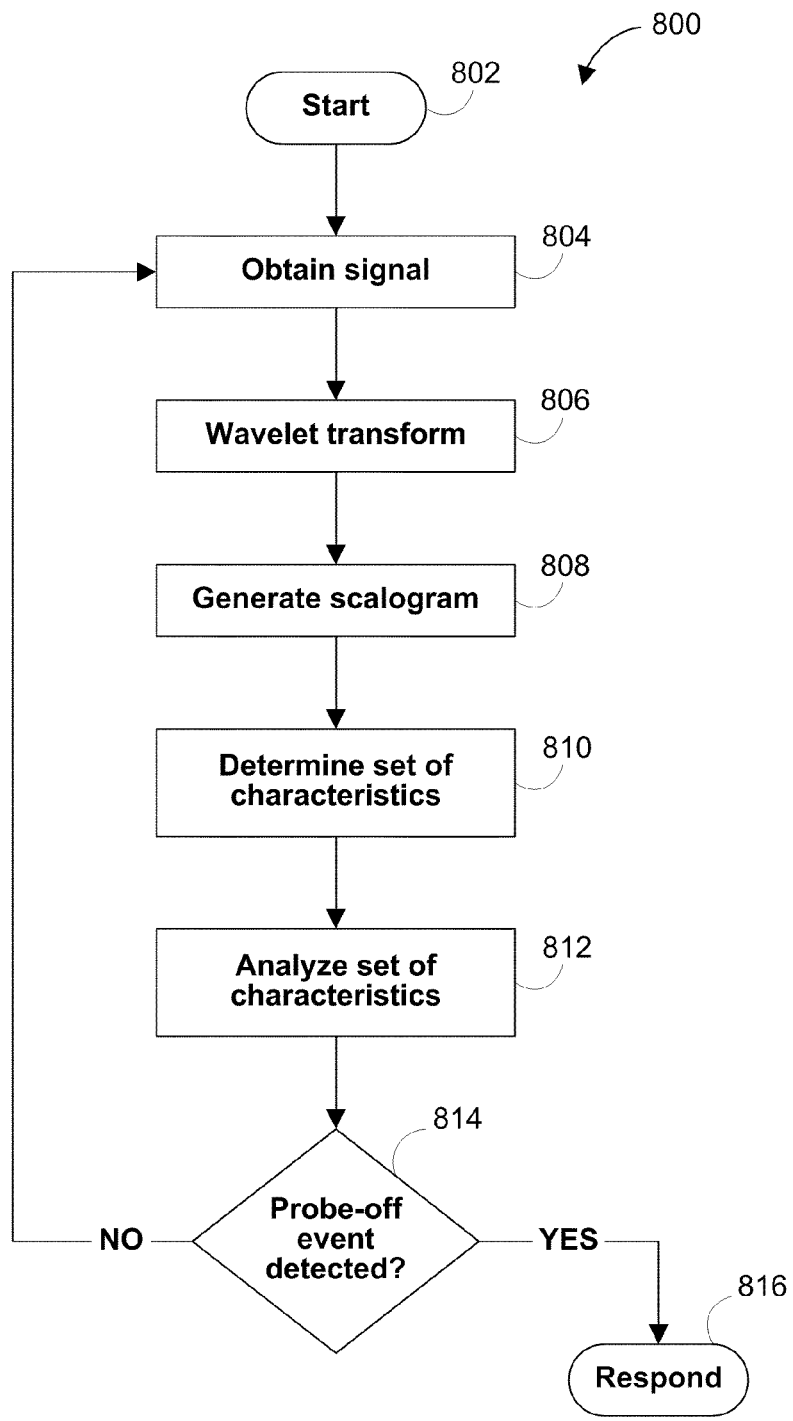
FIG. 8 is a flow chart of an illustrative process for determining and responding to the existence of a probe-off event in accordance with an embodiment.

FIG. 8 is a flow chair of an illustrative process 800 for determining and responding to the existence of a probe-off event in accordance with an embodiment. Process 800 may begin at step 802. At step 804, a portion of a suitable signal may be obtained using, for example, using pulse oximetry system 10 (FIGS. 1 and 2) or system 400 (FIG. 4). The signal may be obtained from a target stimulus provided by a patient. The signal obtained may be a PPG signal or any other suitable signal. For example, the signal obtained may be another biosignal (such as a electrocardiogram, ectroencephalogram, electrogastrogram, electromyogram, heart rate, pathological sound, ultrasound, or any other suitable biosignal), dynamic signal, non-destructive testing signal, condition monitoring signal, fluid signal, geophysical signal, astronomical signal, electrical signal, financial signal including a financial index signal, sound and speech signal, chemical signal, meteorological signal including a climate signal, and/or any other suitable signal, and/or any combination thereof.

At step 806, the wavelet transform of the signal may be obtained. Such a wavelet transform may be obtained, for example, by system 10 (FIGS. 1 and 2) or system 400 (FIG. 4). At step 808, the scalogram of the wavelet transform may be generated or otherwise obtained using, for example a processor. For example, the scalogram of the wavelet transform may be generated or obtained using a processor such as processor 412 (FIG. 4) or microprocessor 48 (FIG. 2). In addition to the scalogram, other parts of the wavelet transform may be inspected to determine whether a probe-off event has occurred. For example, the transform modulus, phase, real, and/or imaginary parts may be generated at step 808 in place of or in addition to the scalogram. Each of these features may then be used, either singly or in combination, in the subsequent steps of process 800.

At step 810, one or more characteristics of the scalogram obtained in step 808 may be determined using a processor. One or more of the characteristics that is determined may be chosen to be beneficial in determining if a probe-off event has occurred. For example, the characteristics that may be chosen for inclusion may be based on: detecting for the presence or absence of certain features in the scalogram (features may include pulse band 610 (FIG. 6), low-frequency information pattern 612 (FIG. 6), regular, repeated high-scale pattern 614 (FIG. 6), or one or more other suitable features), calculating numerical values, estimating certain features, or any other suitable criteria. Example characteristics include: a region of a certain area having at least a certain minimum energy level at all locations, the energy level averaged across scale values for each time instant, or the fraction of an area that has an energy level above a certain threshold.

Additionally, in determining each characteristic, a probability or confidence indicator may be computed, for example by processor 412 (FIG. 4) or by microprocessor 48 (FIG. 2), and included in the determination. A probability may represent the statistical probability or fraction of the time for which the characteristic is correctly determined. Similarly, a confidence indicator may represent the degree of confidence that a characteristic has been correctly determined, and may be measured, for example, using an estimation technique such a minimum mean square error. If the characteristic to be determined is a binary determination, such as in determining either the presence or absence of a feature, the probability or confidence indicator may correspond to, for example, the probability or the confidence indicator that the decision is correct. Such a probability or confidence indicator may be determined using, for example, Bayesian or Neyman-Pearson statistical techniques computed in processor 412 (FIG. 4), historical or trend data preloaded or otherwise available in monitor 14 (FIG. 1), patient specific medical information provided to monitor 14 (FIG. 1) using user inputs 56 (FIG. 2), or another other suitable method. The use of probability or confidence indicator information will be further illustrated in FIGS. 10(a)-10(e).

Step 810 may incorporate the use of past scalogram data that has been obtained in previous iterations of process 800 in determining characteristics. For example, new scalogram data may be generated each time step 808 is performed. This past scalogram data may be stored in, for example, ROM 52 (FIG. 2) and/or RAM 54 (FIG. 2) for use during each subsequent iteration of step 808. This past information may be used separately or together with current scalogram data to determine characteristics as well as determine probability or confidence indicators.

At step 812, the characteristics determined in step 810 may be analyzed. Analyzing the characteristics may generally involve parsing, combining, or weighing individual results obtained in step 810 so that a single, overall decision may be made as to whether a probe-off event has occurred. For example, if one or more characteristics, along with probability or confidence indicator information, was determined in step 810, in step 812 these individual characteristics (for example, whether the pulse band 610 (FIG. 6), low-frequency information pattern 612 (FIG. 6), and regular, repeated high-scale pattern 614 (FIG. 6) were detected present or absent) may be combined to produce data that may be used to make a single overall decision. Any suitable parsing, combining, or weighing strategy may be used. For example, maximum-likelihood techniques may be used to combine data when the prior probability of a probe-off event is known, and Neyman-Pearson combining techniques may be used when the prior probability of a probe-off event is unknown. Additional weighing techniques may include: Bayesian probability distribution function estimation, genetic programming, genetic algorithms, and neural networks for the adaptive learning of decision boundaries. Alternatively fuzzy logic, modal logic or predicate calculus may be used for the syntactic processing of multiple data points. Multiple data points may also be characterized by way of learning vector quantization (LVQ) methods such as Kohonen networks. In addition, majority-vote decision rules may be used to determine if a probe-off event has occurred At step 814, a decision may be made as to whether a probe-off event has been occurred or been detected. Such a decision may be made based on the output of step 812. If it is determined that a probe-off event has occurred, a response is initiated in step 816. A response may include many features singly or in combination. For example, possible features may include generating an audible alert or alarm that is emitted, for example, using speaker 22 (FIG. 2) as well as possibly through other audio devices, generating an on-screen message, for example, on display 20 (FIG. 1) or display 28 (FIG. 1), generating a pager message, a text message, or a phone call, for example, using a wireless connection embedded or attached to a system such as system 10 (FIG. 1), activating a secondary or backup sensor or sensor array, for example, connected through a wire or wirelessly to monitor 14 (FIG. 1), or regulating the automatic administration medicine, for example, which is controlled in part or fully through a system such as system 10 (FIG. 1). If it is determined that a probe-off event has not occurred, then process 800 returns to step 804 and the "next" portion of the signal is obtained. The next portion of the signal may start where the previously read signal ended, overlap with the previously read signal, or be located at some distance in the future from the previously read signal. In any of these or in other scenarios, the choice of the signal region to be selected could be influenced by the data determined in step 810 or analyzed in step 812.

Figure 9:
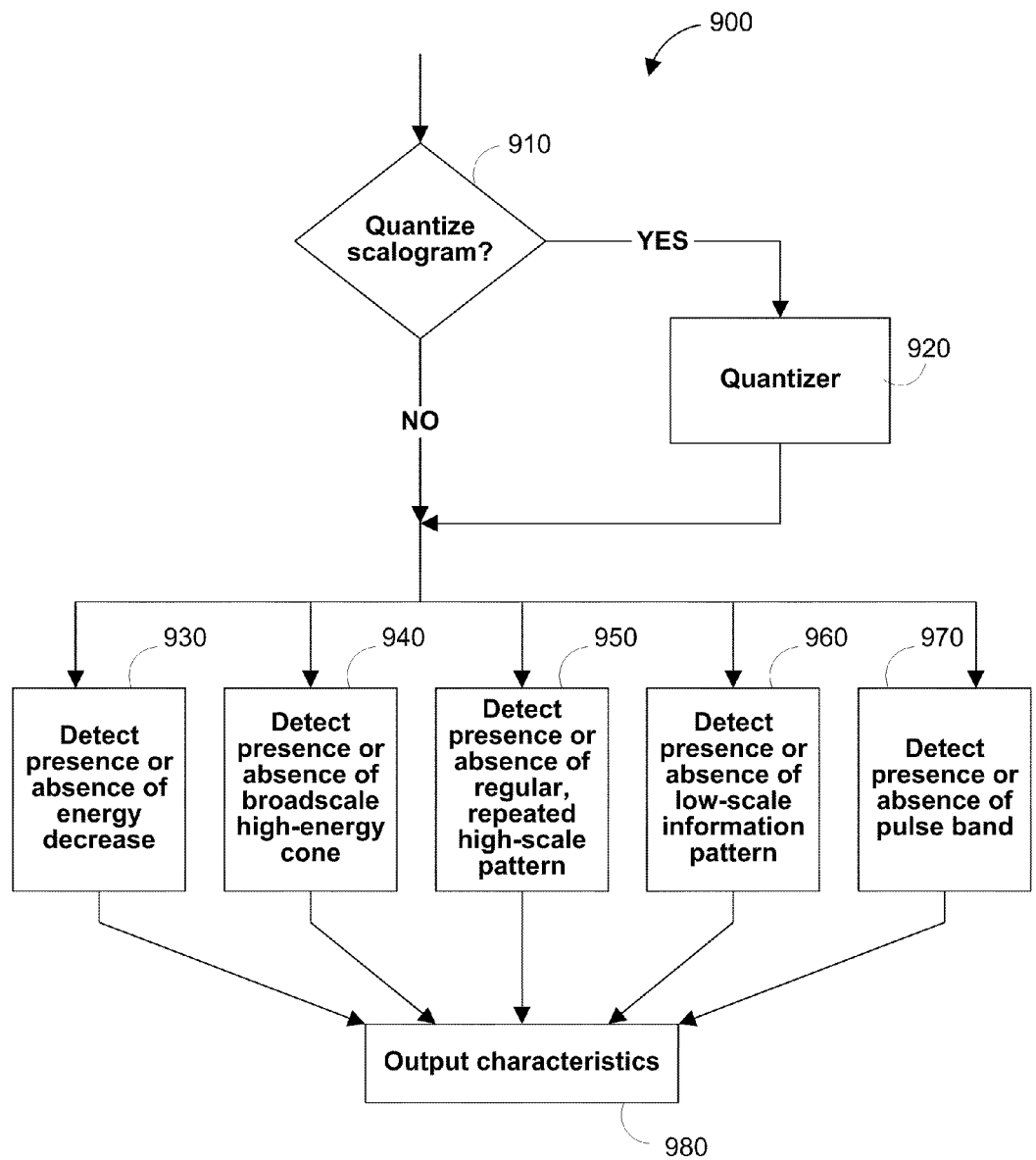
FIG. 9 is a flow chart of an illustrative process for determining one or more of scalogram characteristics in accordance with an embodiment.

FIG. 9 shows a flow chart of an illustrative process for determining one or more scalogram characteristics 810 (FIG. 8) in accordance with an embodiment. At step 910 a decision may be made whether to quantize the scalogram determined in step 808 (FIG. 8). For example, this decision may be preprogrammed in a system such as system 10 (FIG. 1) or it may be made using user inputs 56 (FIG. 2). The factors and tradeoffs that are relevant to such a decision may include: the computational resources available to perform the quantization, for example, using processor 412 (FIG. 4) or microprocessor 48 (FIG. 2), the tolerable delay and/or error-rate in detecting the probe-off event, as well as any combination of these and other factors. Also, each threshold may be a variable quantity that varies with, for example, the time or scale value. At step 920, the scalogram may be processed, producing a quantized scalogram. The scalogram may be processed, for example using system 400 (FIG. 4), processor 412 (FIG. 4), and/or microprocessor 48 (FIG. 2). In steps 930, 940, 950, 960, and 970, characteristics that may be relevant to the detection of a probe-off event are determined, as will be described below. We emphasize that any of the steps 930, 940, 950, 960, or 970, taken individually or in any suitable combination, may be sufficient for the detection of a probe-off event, and is a valid embodiment of step 810 (FIG. 8). In FIG. 9, we illustrate one particular embodiment in which each of the steps 930, 940, 950, 960, and 970 are incorporated into step 810 (FIG. 8).

Figure 10A:
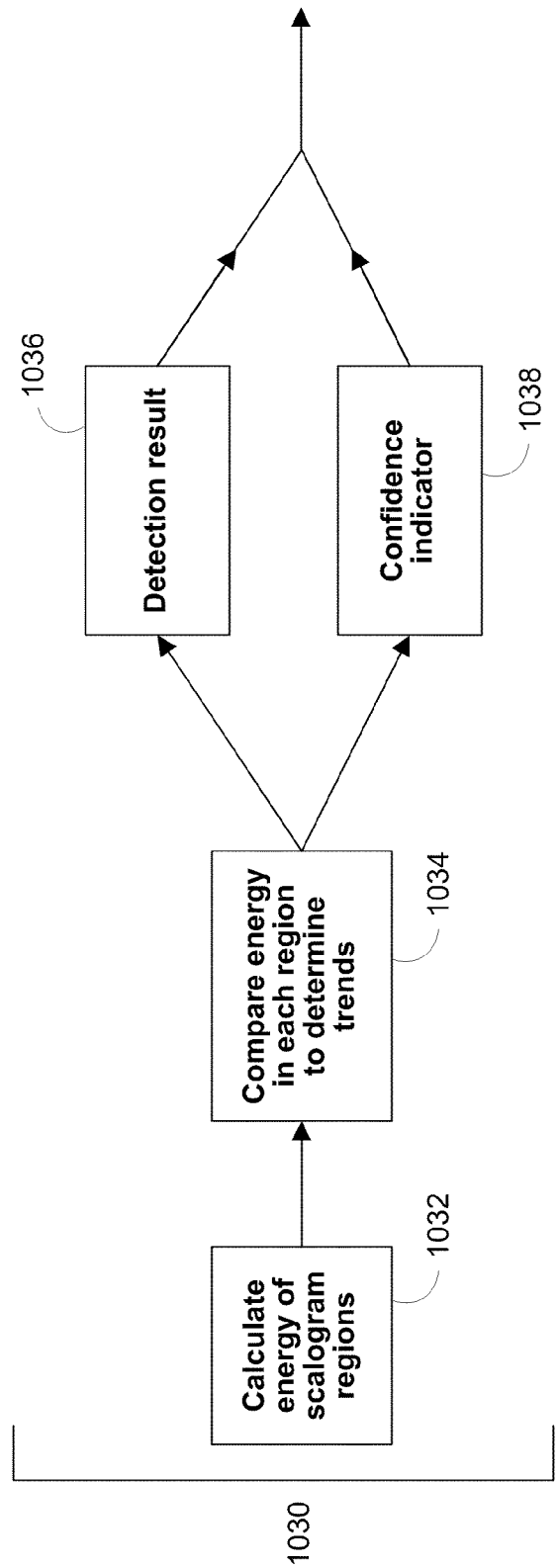
FIG. 10(a) shows an illustrative process for detecting the presence or absence of an energy decrease in accordance with an embodiment.

At step 930, the presence or absence of an energy decrease may be detected by a suitable detection process that may be run, for example, in system 400 (FIG. 4) or in processor 412 (FIG. 4). Such a process may return both a binary decision (i.e., "detected" or "not detected") along with a probability or confidence indicator. The detection process may use both past and current scalogram data to perform the detection. To detect the presence or absence of the energy decrease, any suitable technique may be used. For example, one illustrative process for detecting the presence or absence of an energy decrease is shown in FIG. 10(a). At step 1032, the detection process may calculate the energy of scalogram regions by dividing the current and past scalograms into numerous local regions that may or may not overlap in time and/or scale values. The size, number, and identification of regions may be based on many factors including: the speed of processor 412 (FIG. 4), the amount of ROM 52 (FIG. 2) and/or RAM 54 (FIG. 2), and the degree of accuracy required in performing detection. At step 1034 (FIG. 10(a)), the detection process may compare the average energy, minimum energy, maximum energy, or any combination of these and other energy characteristics in each area to determine trends about the energy level. The energy characteristics may be averaged over a period or range of time to minimize the effect of short term changes in energy levels. At step 1036 (FIG. 10(a)), the detection process may produce a detection result. For example, the detection result may be a binary decision as to whether the energy decrease is present or absent. A decision may be made, for example, if the change is greater than a fixed or dynamic threshold. At step 1038 (FIG. 10(a)), the detection process may produce a confidence indicator based on, for example, the number and area of regions tabulated, and on the magnitude of an apparent energy decrease. The foregoing example process is merely illustrative and any suitable modifications may be made.

Figure 10B:
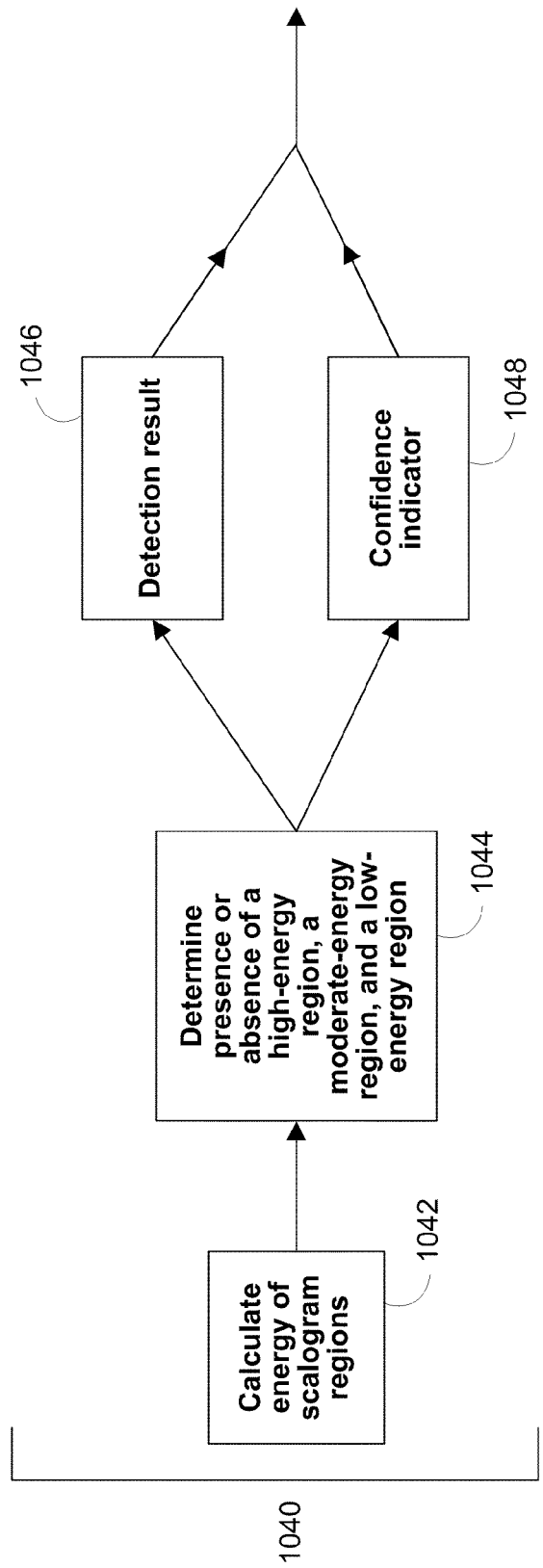
FIG. 10(b) shows an illustrative process for detecting the presence or absence of a broadscale high-energy cone in accordance with an embodiment.

Referring back to FIG. 9, at step 940, the presence or absence of the broadscale high-energy cone 606 (FIG. 6) may be detected by a suitable detection process that may be run, for example, in system 400 (FIG. 4) or in processor 412 (FIG. 4). Such a process may return both a binary decision (i.e., "detected" or "not detected") along with a probability or confidence indicator. The detection process may use both past and current scalogram data to perform the detection. To detect the presence or absence of the broadscale high-energy cone 606 (FIG. 6) any suitable techniques may be used. For example, one illustrative process for detecting the presence or absence of the broadscale high-energy cone 606 (FIG. 6) is shown in FIG. 10(b). At step 1042 (FIG. 10(b)), the detection process may calculate the energy of scalogram regions by dividing the current and past scalograms or scalogram data into one or more local regions that may or may not overlap in time and/or scale values. The size, number, and identification of regions may be based on many factors including: the speed of processor 412 (FIG. 4), the amount of ROM 52 (FIG. 2) and/or RAM 54 (FIG. 2), and the degree of accuracy required in performing detection. At step 1044 (FIG. 10(b)), the detection process may search in time for a region of moderate energy, followed by a region of high-energy, followed by a region of moderate or low-energy. Further, the detection process may sample the width of the high-energy region at various scale values. At step 1046 (FIG. 10(b)), the detection process may produce a detection result. For example, the detection result may be a binary decision as to whether a broadscale high-energy cone such as the broadscale high-energy cone in 606 (FIG. 6) is present or absent. At step 1048 (FIG. 10(b)), the detection process may produce a confidence indicator based on, for example, the magnitude of energy fluctuations and on the degree to which the high-energy region resembles a cone shape as a function of the scale value. The foregoing example process is merely illustrative and any suitable modifications may be made.

Figure 10C:
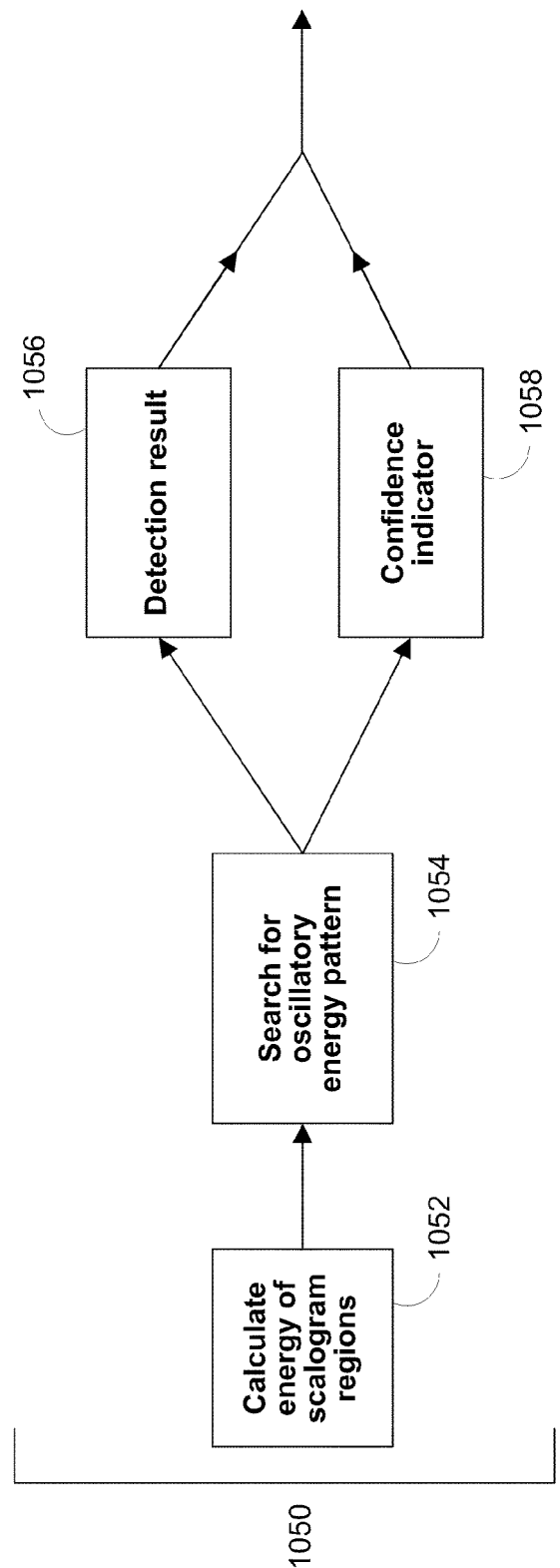
FIG. 10(c) shows an illustrative process for detecting the presence or absence of a regular, repeated high-scale pattern in accordance with an embodiment.

Referring back to FIG. 9, at step 950, the presence or absence of the regular, repeated high-scale pattern 614 (FIG. 6) may be detected by a suitable detection process that may be run, for example, in system 400 (FIG. 4) or in processor 412 (FIG. 4). Such a process may return both a binary decision (i.e., "detected" or "not detected") along with a probability or confidence indicator. The detection process may use both past and current scalogram data to perform the detection. To detect the presence or absence of the regular, repeated high-scale pattern 614 (FIG. 6) any suitable technique may be used. For example, one illustrative process for detecting the presence or absence of the regular, repeated high-scale pattern 614 (FIG. 6) is shown in FIG. 10(c). At step 1052 (FIG. 10(c)), the detection process may calculate the energy of scalogram regions by dividing the current and past scalograms into numerous local regions that may or may not overlap in time and/or scale values. The size, number, and identification of regions may be based on many factors including: the speed of processor 412 (FIG. 4), the amount of ROM 52 (FIG. 2) and/or RAM 54 (FIG. 2), and the degree of accuracy required in performing detection. At step 1054 (FIG. 10(c)), the detection process may search one or more known scale ranges for an energy pattern that rapidly oscillates in time between moderate and high-energy values. At step 1056 (FIG. 10(c)), the detection process may produce a detection result. For example, the detection result may be a binary decision as to whether the regular, repeated high-scale pattern 614 (FIG. 6) is present or absent. At step 1058 (FIG. 10(c)), the detection process may produce a confidence indicator based on, for example, the change in or separation between energy values, the frequency of oscillation, and the scale values over which the pattern occurs. The foregoing example process is merely illustrative and any suitable modifications may be made.

Figure 10D:
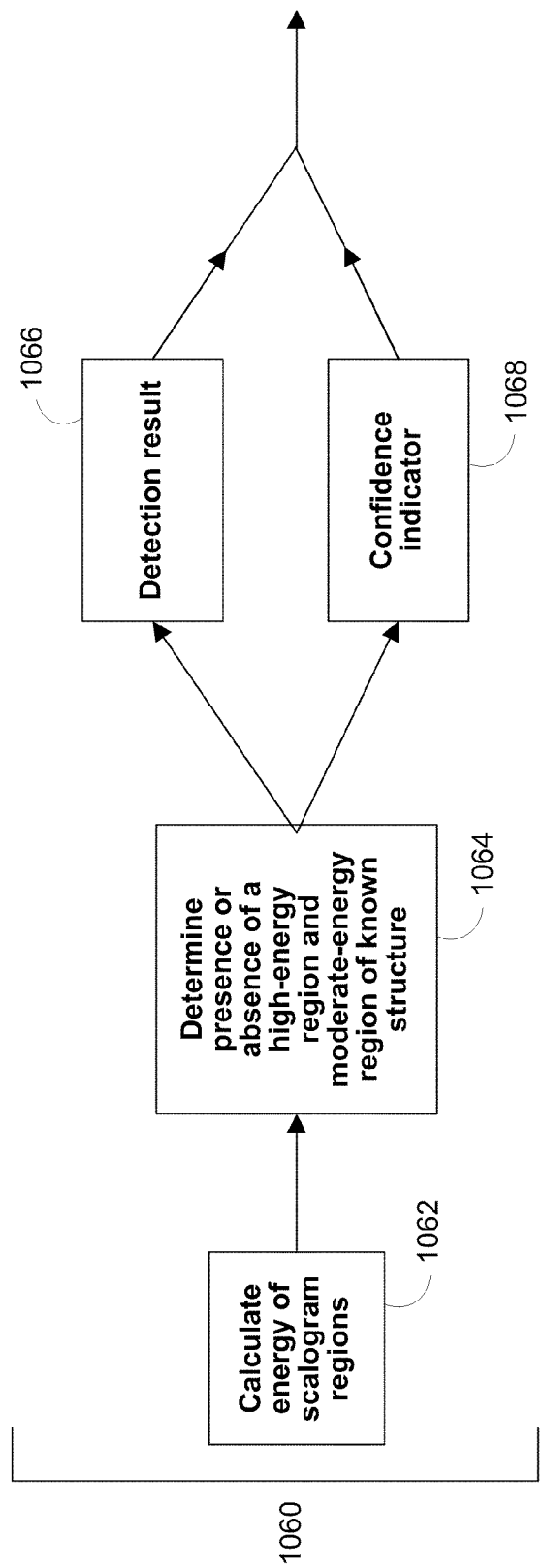
FIG. 10(d) shows an illustrative process for detecting the presence or absence of a low-scale information pattern in accordance with an embodiment.
Figure 10E:
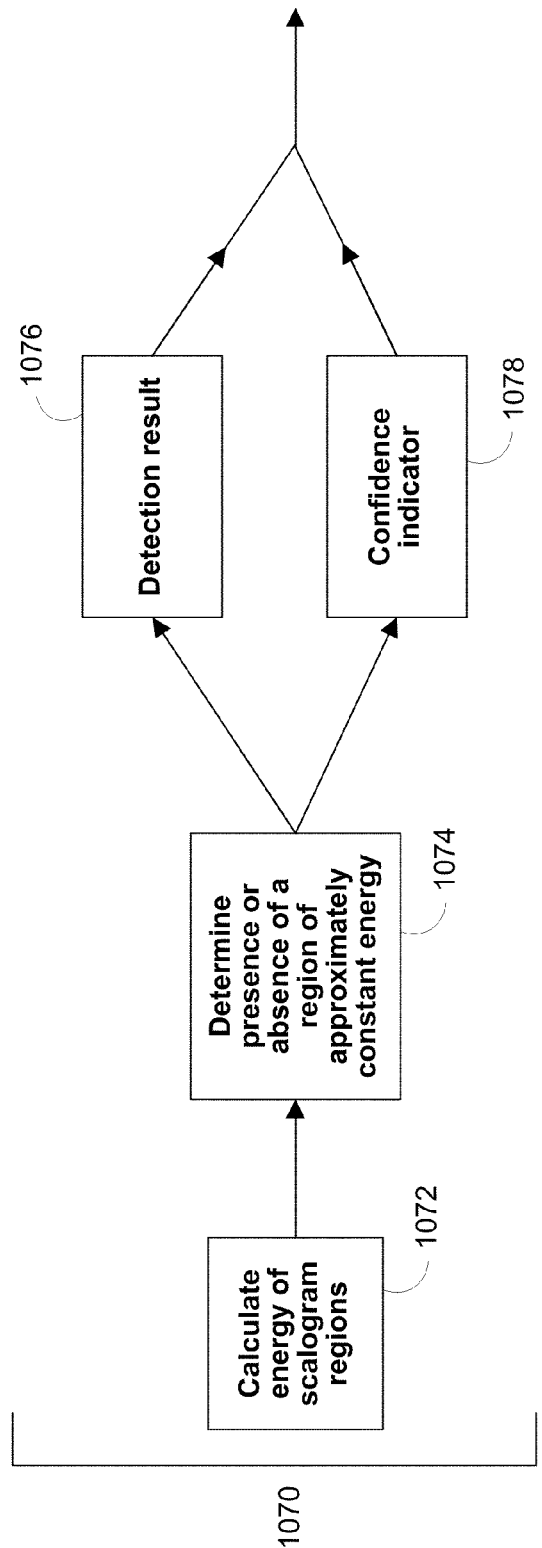
FIG. 10(e) shows an illustrative process for detecting the presence or absence of a pulse band in accordance with an embodiment.

Referring back to FIG. 9, at step 960, the presence or absence of the low-scale information pattern 612 (FIG. 6) may be detected by a suitable detection process that may be run, for example, in system 400 (FIG. 4) or in processor 412 (FIG. 4). Such a process may return both a binary decision (i.e., "detected" or "not detected") along with a probability or confidence indicator. The detection process may use both past and current scalogram data to perform the detection. To detect the presence or absence of the low-scale information pattern 612 (FIG. 6) any suitable technique may be used. For example, one illustrative process for detecting the presence or absence of low-scale information pattern 612 (FIG. 6) is shown in FIG. 10(d). At step 1062 (FIG. 10(d)), the detection process may calculate the energy of scalogram regions by dividing the current and past scalograms into one or more local regions that may or may not overlap in time and/or scale values. The size, number, and identification of regions may be based on many factors including: the speed of processor 412 (FIG. 4), the amount of ROM 52 (FIG. 2) and/or RAM 54 (FIG. 2), and the degree of accuracy required in performing detection. At step 1064 (FIG. 10(*d*)), the detection process may search for a region of very high-energy followed by a region of moderate energy as the scale value is decreased. Alternatively, the detection process may search for very high-energy region followed by a low energy region to reduce the probability of mistakenly detecting an artifact in place of a true probe-off event (an artifact may create the appearance of a region with properties similar to region 604 (FIG. 6) within region 608 (FIG. 6). The process could also calculate, within the region of low or moderate-energy, the degree to which the energy structure matches a known energy structure (e.g., a respiration band), based on statistical techniques. At step 1066 (FIG. 10(*d*)), the detection process may produce a detection result. For example, the detection result may be a binary decision as to whether the low-scale information pattern 612 (FIG. 6) is present or absent. At step 1068 (FIG. 10(*d*)), the detection process may produce a confidence indicator based on, for example, the degree to which the apparent low-scale information pattern 612 (FIG. 6) approximates a known energy structure. The foregoing example process is merely illustrative and any suitable modifications may be made.

Referring back to FIG. 9, at step 970, the presence or absence of the pulse band may be detected by a suitable detection process that may be run in system 400 (FIG. 4) or in processor 412 (FIG. 4). Such a process may return both a binary decision (i.e., "detected" or "not detected") along with a probability or confidence indicator. The detection process may use both past and current scalogram data to perform the detection. To detect the presence or absence of the pulse band many suitable techniques may be used. For example, one illustrative process for detecting the presence or absence of pulse band 610 (FIG. 6) is shown in FIG. 10(*e*). At step 1072 (FIG. 10(*e*)), the detection process may calculate the energy of scalogram regions by dividing the current and past scalograms into numerous local regions that may or may not overlap in time and/or scale values. The size, number, and identification of regions may be based on many factors including: the speed of processor 412 (FIG. 4), the amount of ROM 52 (FIG. 2) and/or RAM 54 (FIG. 2), and the degree of accuracy required in performing detection. At step 1074 (FIG. 10(*e*)), the detection process may search a range of known scale values for a region of approximately constant energy, and may tabulate the possible ending point of such a region (if such a region is found). Alternatively or in addition to the foregoing, the pulse band may be identified using ridge following techniques. At step 1076 (FIG. 10(*e*)), the detection process may produce a detection result. For example, the detection result may be a binary decision as to whether the pulse band is present or absent. At step 1078 (FIG. 10(*e*)), the detection process may produce a confidence indicator based on, for example, the magnitude of energy values and the range of scale values over which the apparent pulse band 610 (FIG. 6) is detected. The foregoing example process is merely illustrative and any suitable modifications may be made.

Referring back to FIG. 9, at step 980 the detection results and confidence information may be aggregated and passed to step 812 (FIG. 8) and analyzed to determine if a probe-off event has occurred as discussed above.

Figure 11:
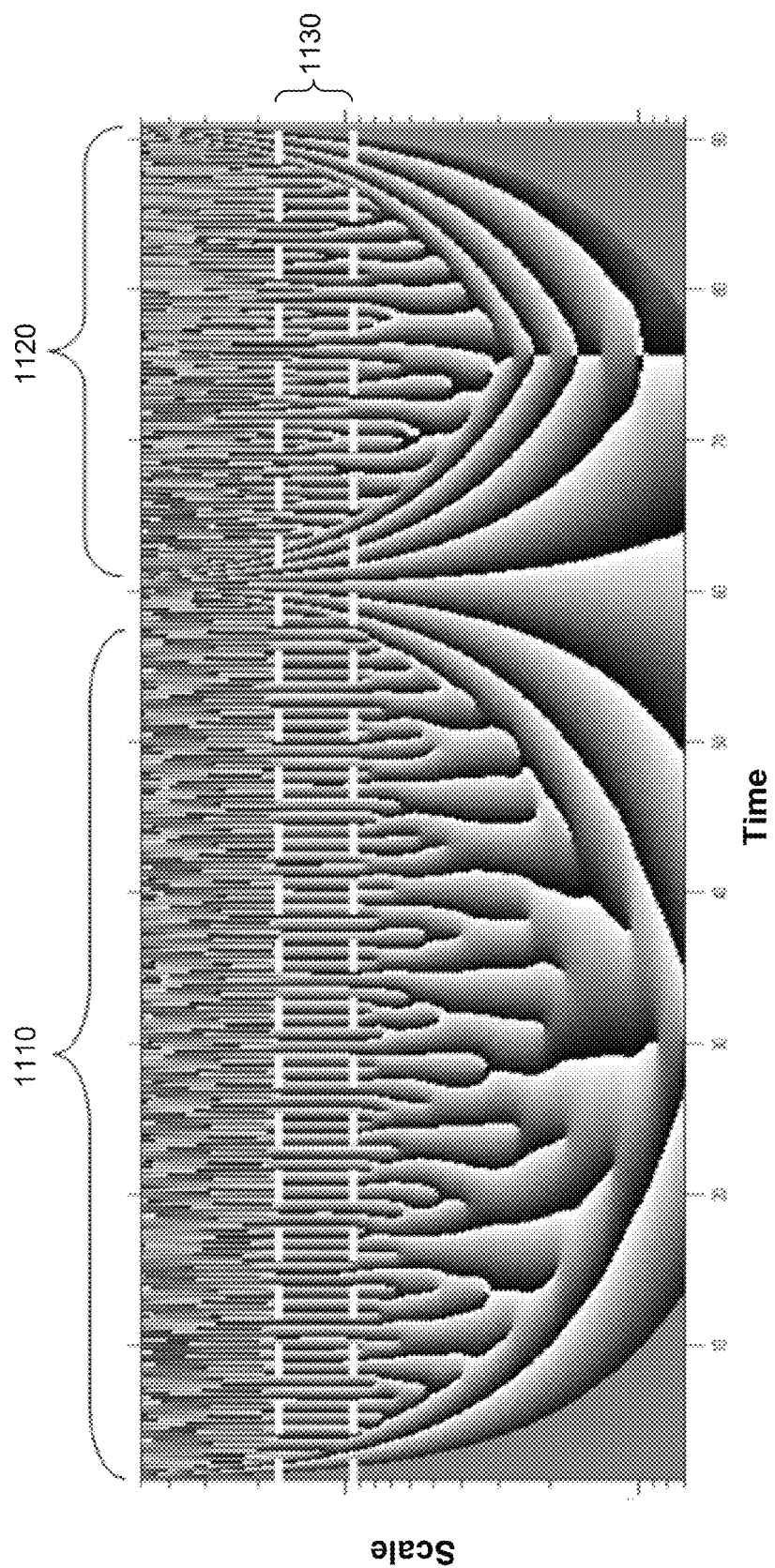
FIG. 11 shows an illustrative phase plot derived from the PPG signal of FIG. 5 in accordance with an embodiment.

FIG. 11 shows an illustrative phase plot derived from PPG signal 502 (FIG. 5) in accordance with an embodiment. Time period 1110 corresponds to the time period before the probe-off event, and time period 1120 corresponds to the time period after the probe-off event corresponding to PPG signal 502 (FIG. 5). Regular phase cycling is observed in pulse band 1130 during time period 1110. However, in time period 1120, the phase cycle is characterized by an irregular pattern. By monitoring the regularity and/or a change in the regularity of the phase cycling in pulse band 1130, the probe-off event may be detected. Alternatively, the phase in other regions of the plot may be used to determine the probe-off event. For example, the regularity of phase cycling in the respiration band may also be monitored.

Figure 12:
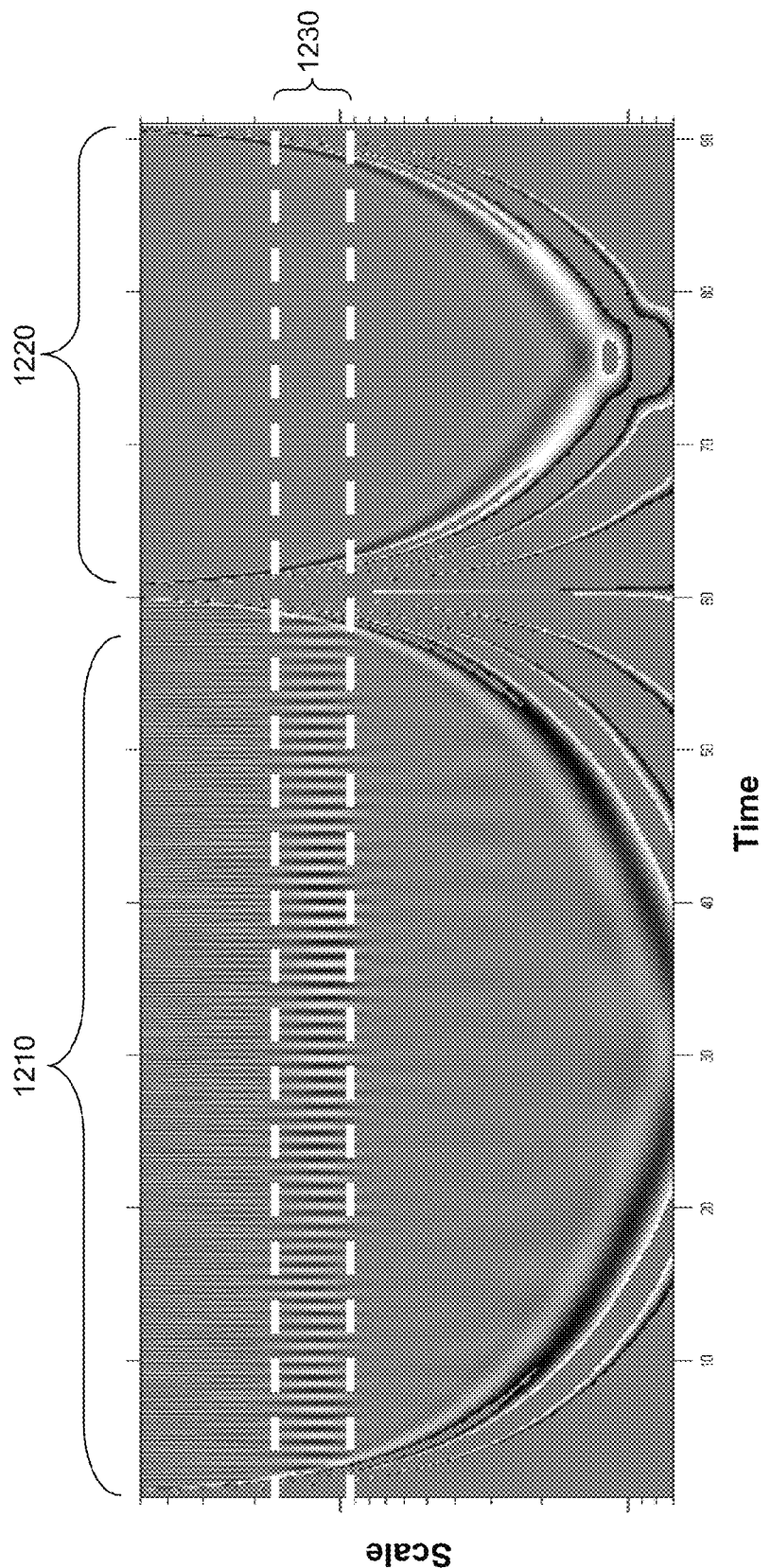
FIG. 12 shows an illustrative plot of the real part of a wavelet transform derived from the PPG signal of FIG. 5 in accordance with an embodiment.

FIG. 12 shows an illustrative plot of the real part of a wavelet transform derived from PPG signal 502 (FIG. 5). Time period 1210 corresponds to the time period before the probe-off event, and time period 1220 corresponds to the time period after the probe-off event corresponding to PPG signal 502 (FIG. 5). In time period 1210, regular undulations in pulse band 1230 are observed. However, in the amplitude and regularity of the undulations diminish significantly in time period 1220. The amplitude and regularity of undulations in pulse band 1230 may be used to detect the probe-off event. Additionally, the imaginary part of the wavelet transform derived from PPG signal 502 (FIG. 5) may be used to detect the probe drop off event by monitoring the amplitude and regularity of undulations in pulse band. Further any suitable combination of the techniques described above may be used to determine the probe-off event.

It will also be understood that the above method may be implemented using any human-readable or machine-readable instructions on any suitable system or apparatus, such as those described herein.

The foregoing is merely illustrative of the principles of this disclosure and various modifications may be made by those skilled in the art without departing from the scope and spirit of the disclosure. The following claims may also describe various aspects of this disclosure.

What is claimed is:

1. A method of detecting a probe-off event comprising:
   obtaining a signal;
   generating, using processing equipment, a wavelet transform based at least in part on the signal;
   generating, using the processing equipment, a scalogram based at least in part on the wavelet transform;
   determining, using the processing equipment, one or more characteristics from the scalogram;
   analyzing, using the processing equipment, the one or more characteristics; and
   detecting, using the processing equipment, a probe-off event based at least in part on the one or more characteristics.

2. The method of claim 1, wherein obtaining the signal comprises obtaining a PPG signal.

3. The method of claim 1, further comprising quantizing, using the processing equipment, the scalogram prior to determining the one or more characteristics.

4. The method of claim 1, wherein determining the one or more characteristics comprises detecting, using the processing equipment, the presence or absence of the one or more characteristics in the scalogram.

5. The method of claim 4, further comprising:
   detecting, using the processing equipment, regularity in the scalogram at one or more times prior to the presence of a characteristic; and
   detecting, using the processing equipment, non-regularity in the scalogram at one or more times subsequent to the presence of the characteristic.

6. The method of claim 5, wherein the one or more characteristics comprise characteristics selected from the group consisting of an energy decrease, a broadscale high-energy cone, a regular, repeated high-scale pattern, a low-scale information pattern, a pulse band, and combinations thereof.

7. The method of claim 6, wherein detecting the presence of the broadscale high-energy cone comprises:
calculating, using the processing equipment, energy within a first region of the scalogram over time;
calculating, using the processing equipment, energy within a second region of the scalogram over time; and
detecting, using the processing equipment, a change in the energy calculated in the second region compared to the energy calculated in the first region.

8. The method of claim 6, wherein detecting the probe-off event comprises detecting the probe-off event when a broadscale high-energy cone is detected and at least one of the following events occurs: an energy decrease is detected; a regular repeating high-scale pattern is absent after the occurrence of the broadscale high energy cone; a low-scale information pattern is absent after the occurrence of the broadscale high energy cone; and the pulse band is absent after the occurrence of the broadscale-high energy cone.

9. The method of claim 1, further comprising calculating, using the processing equipment, a confidence indicator related to the probe-off event.

10. A system for detecting a probe-off event comprising:
a processor configured to perform operations comprising:
obtaining a signal;
generating a wavelet transform based at least in part on the signal;
generating a scalogram based at least in part on the wavelet transform;
determining one or more characteristics from the scalogram;
analyzing the one or more characteristics; and
detecting a probe-off event based at least in part on the one or more characteristics.

11. The system of claim 10, wherein obtaining the signal comprises obtaining a PPG signal.

12. The system of claim 10, wherein the processor is further configured to quantize the scalogram prior to determining the one or more characteristics.

13. The system of claim 10, wherein determining the one or more characteristics comprises detecting the presence or absence of the one or more characteristics in the scalogram.

14. The system of claim 13, wherein the processor is further configured to perform operations comprising:
detecting regularity in the scalogram at one or more times prior to the presence of a characteristic; and
detecting non-regularity in the scalogram at one or more times subsequent to the presence of the characteristic.

15. The system of claim 14, wherein the one or more characteristics comprise characteristics selected from the group consisting of an energy decrease, a broadscale high-energy cone, a regular, repeated high-scale pattern, a low-scale information pattern, a pulse band, and combinations thereof.

16. The system of claim 15, wherein detecting the presence of the broadscale high-energy cone comprises:
calculating energy within a first region of the scalogram over time;
calculating energy within a second region of the scalogram over time; and
detecting a change in the energy calculated in the second region compared to the energy calculated in the first region.

17. The system of claim 15, wherein detecting the probe-off event comprises detecting the probe-off event when a broadscale high-energy cone is detected and at least one of the following events occurs: an energy decrease is detected; a regular repeating high-scale pattern is absent after the occurrence of the broadscale high energy cone; a low-scale information pattern is absent after the occurrence of the broadscale high energy cone; and the pulse band is absent after the occurrence of the broadscale-high energy cone.

18. The system of claim 10, wherein the processor is further configured to calculate a confidence indicator related to the probe-off event.

19. A non-transitory computer-readable medium for detecting a probe-off event, the computer-readable medium having computer program instructions recorded thereon for:
obtaining a signal;
generating a wavelet transform based at least in part on the signal;
generating a scalogram based at least in part on the wavelet transform;
determining one or more characteristics from the scalogram; analyzing the one or more characteristics; and
detecting a probe-off event based at least in part on the one or more characteristics.

20. The non-transitory computer-readable medium of claim 19, having further computer program instructions for determining the one or more characteristics at least in part by detecting the presence or absence of the one or more characteristics in the scalogram.

* * * * *